(12) United States Patent
Miesel et al.

(10) Patent No.: US 8,308,661 B2
(45) Date of Patent: Nov. 13, 2012

(54) COLLECTING ACTIVITY AND SLEEP QUALITY INFORMATION VIA A MEDICAL DEVICE

(75) Inventors: Keith A. Miesel, St. Paul, MN (US); Kenneth T. Heruth, Edina, MN (US); Jonathan C. Werder, Corcoran, MN (US); Steve R. LaPorte, San Antonio, TX (US); Nina M. Graves, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 1418 days.

(21) Appl. No.: 11/691,425

(22) Filed: Mar. 26, 2007

(65) Prior Publication Data

US 2008/0071150 A1 Mar. 20, 2008

Related U.S. Application Data

(63) Continuation-in-part of application No. 11/081,857, filed on Mar. 16, 2005, now abandoned, which is a continuation-in-part of application No. 10/825,955, filed on Apr. 15, 2004, now Pat. No. 7,491,181.

(60) Provisional application No. 60/553,785, filed on Mar. 16, 2004, provisional application No. 60/785,662, filed on Mar. 24, 2006.

(51) Int. Cl.
*A61B 5/103* (2006.01)
*A61B 5/117* (2006.01)
*A61B 5/04* (2006.01)

(52) U.S. Cl. ........................ 600/587; 600/544

(58) Field of Classification Search .................. 600/587, 600/595, 544
See application file for complete search history.

(56) References Cited

U.S. PATENT DOCUMENTS

| | | | |
|---|---|---|---|
| 4,297,685 | A | 10/1981 | Brainard, II |
| 4,550,736 | A | 11/1985 | Broughton et al. |
| 4,771,780 | A | 9/1988 | Sholder |
| 4,776,345 | A | 10/1988 | Cohen et al. |
| 4,846,195 | A | 7/1989 | Alt |
| 5,040,536 | A | 8/1991 | Riff |
| 5,058,584 | A | 10/1991 | Bourgeois |
| 5,125,412 | A | 6/1992 | Thornton |

(Continued)

FOREIGN PATENT DOCUMENTS

DE 198 31 109 1/2000

(Continued)

OTHER PUBLICATIONS

Office Action dated Oct. 14, 2009 for U.S. Appl. No. 11/081,857 (14 pgs.).

(Continued)

*Primary Examiner* — Jeffrey G Hoekstra
(74) *Attorney, Agent, or Firm* — Shumaker & Sieffert, P.A.

(57) ABSTRACT

A device, such as an implantable medical device (IMD), programming device, or other computing device determines when a patient is attempting to sleep. When the device determines that the patient is attempting to sleep, the device determines values for one or more metrics that indicate the quality of a patient's sleep based on at least one physiological parameter of the patient. When the device determines that the patient is not attempting to sleep, the device periodically determines activity levels of the patient. Activity metric values may be determined based on the determined activity levels. A clinician may use sleep quality information and patient activity information presented by a programming device to, for example, evaluate the effectiveness of therapy delivered to the patient by a medical device.

12 Claims, 16 Drawing Sheets

U.S. PATENT DOCUMENTS

| | | |
|---|---|---|
| 5,154,180 A | 10/1992 | Blanchet et al. |
| 5,233,984 A | 8/1993 | Thompson |
| 5,275,159 A | 1/1994 | Griebel |
| 5,335,657 A | 8/1994 | Terry, Jr. et al. |
| 5,337,758 A | 8/1994 | Moore et al. |
| 5,342,409 A | 8/1994 | Mullett |
| 5,469,861 A | 11/1995 | Piscopo et al. |
| 5,476,483 A | 12/1995 | Bornzin et al. |
| 5,514,162 A | 5/1996 | Bornzin et al. |
| 5,593,431 A | 1/1997 | Sheldon |
| 5,622,428 A | 4/1997 | Bonnet |
| 5,645,053 A | 7/1997 | Remmers et al. |
| 5,732,696 A | 3/1998 | Rapoport et al. |
| 5,782,884 A | 7/1998 | Stotts et al. |
| 5,814,093 A | 9/1998 | Stein |
| 5,851,193 A | 12/1998 | Arikka et al. |
| 5,895,371 A | 4/1999 | Levitas et al. |
| 5,904,708 A | 5/1999 | Goedeke |
| 5,919,149 A | 7/1999 | Allum |
| 5,941,906 A | 8/1999 | Barreras, Sr. et al. |
| 5,944,680 A | 8/1999 | Christopherson et al. |
| 5,999,846 A | 12/1999 | Pardey et al. |
| 6,044,297 A | 3/2000 | Sheldon et al. |
| 6,045,513 A | 4/2000 | Stone et al. |
| 6,059,576 A | 5/2000 | Brann |
| 6,091,973 A | 7/2000 | Colla et al. |
| 6,095,991 A | 8/2000 | Krausman et al. |
| 6,102,874 A | 8/2000 | Stone et al. |
| 6,120,467 A | 9/2000 | Schallhorn |
| 6,128,534 A | 10/2000 | Park et al. |
| 6,157,857 A | 12/2000 | Dimpfel |
| 6,165,143 A | 12/2000 | van Lummel |
| 6,259,948 B1 | 7/2001 | Florio et al. |
| 6,273,856 B1 | 8/2001 | Sun et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,315,740 B1 | 11/2001 | Singh |
| 6,351,672 B1 | 2/2002 | Park et al. |
| 6,366,813 B1 | 4/2002 | DiLorenzo |
| 6,416,471 B1 | 7/2002 | Kumar et al. |
| 6,433,690 B2 | 8/2002 | Petelenz et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,514,218 B2 | 2/2003 | Yamamoto |
| 6,539,249 B1 | 3/2003 | Kadhiresan et al. |
| 6,574,507 B1 | 6/2003 | Bonnet |
| 6,605,038 B1 | 8/2003 | Teller et al. |
| 6,611,783 B2 | 8/2003 | Kelly, Jr. et al. |
| 6,659,968 B1 | 12/2003 | McClure |
| 6,687,538 B1 | 2/2004 | Hrdlicka et al. |
| 6,731,984 B2 | 5/2004 | Cho et al. |
| 6,735,474 B1 | 5/2004 | Loeb et al. |
| 6,752,766 B2 | 6/2004 | Kowallik et al. |
| 6,773,404 B2 | 8/2004 | Poezevera et al. |
| 6,819,956 B2 | 11/2004 | DiLorenzo |
| 6,878,121 B2 | 4/2005 | Krausman et al. |
| 6,881,192 B1 | 4/2005 | Park |
| 6,884,596 B2 | 4/2005 | Civelli et al. |
| 6,890,306 B2 | 5/2005 | Poezevera |
| 6,928,324 B2 | 8/2005 | Park et al. |
| 6,964,641 B2 | 11/2005 | Cho et al. |
| 7,162,304 B1 | 1/2007 | Bradley |
| 7,209,787 B2 | 4/2007 | DiLorenzo |
| 7,787,946 B2 | 8/2010 | Stahmann et al. |
| 2001/0031930 A1 | 10/2001 | Roizen et al. |
| 2001/0037067 A1 | 11/2001 | Tchou et al. |
| 2002/0077562 A1 | 6/2002 | Kalgren et al. |
| 2002/0091308 A1 | 7/2002 | Kipshidze et al. |
| 2002/0161412 A1 | 10/2002 | Sun et al. |
| 2002/0169485 A1 | 11/2002 | Pless et al. |
| 2002/0177882 A1 | 11/2002 | DiLorenzo |
| 2002/0193697 A1 | 12/2002 | Cho et al. |
| 2002/0193839 A1 | 12/2002 | Cho et al. |
| 2003/0004423 A1 | 1/2003 | Lavie et al. |
| 2003/0135917 A1 | 7/2003 | Ruane |
| 2003/0139692 A1 | 7/2003 | Barrey et al. |
| 2003/0149457 A1 | 8/2003 | Tcheng et al. |
| 2003/0153953 A1 | 8/2003 | Park et al. |
| 2003/0153955 A1 | 8/2003 | Park et al. |
| 2003/0153956 A1 | 8/2003 | Park et al. |
| 2003/0163059 A1 | 8/2003 | Poezevera et al. |
| 2003/0171791 A1 | 9/2003 | KenKnight et al. |
| 2003/0195588 A1 | 10/2003 | Fischell et al. |
| 2003/0212445 A1 | 11/2003 | Weinberg |
| 2004/0002741 A1 | 1/2004 | Weinberg |
| 2004/0002742 A1 | 1/2004 | Florio |
| 2004/0015103 A1 | 1/2004 | Aminian et al. |
| 2004/0049132 A1 | 3/2004 | Barron et al. |
| 2004/0102814 A1 | 5/2004 | Sorensen et al. |
| 2004/0111040 A1 | 6/2004 | Ni et al. |
| 2004/0111041 A1 | 6/2004 | Ni et al. |
| 2004/0199217 A1 | 10/2004 | Lee et al. |
| 2005/0021103 A1 | 1/2005 | DiLorenzo |
| 2005/0021104 A1 | 1/2005 | DiLorenzo |
| 2005/0039745 A1 | 2/2005 | Stahmann et al. |
| 2005/0042589 A1 | 2/2005 | Hatlestad et al. |
| 2005/0060001 A1 | 3/2005 | Singhal et al. |
| 2005/0061320 A1 | 3/2005 | Lee et al. |
| 2005/0065560 A1 | 3/2005 | Lee et al. |
| 2005/0076908 A1 | 4/2005 | Lee et al. |
| 2005/0080463 A1 | 4/2005 | Stahmann et al. |
| 2005/0085738 A1 | 4/2005 | Stahmann et al. |
| 2005/0113710 A1 | 5/2005 | Stahmann et al. |
| 2005/0119703 A1 | 6/2005 | DiLorenzo |
| 2005/0143617 A1 | 6/2005 | Auphan |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222626 A1 | 10/2005 | DiLorenzo |
| 2005/0222643 A1 | 10/2005 | Heruth et al. |
| 2005/0234514 A1 | 10/2005 | Heruth et al. |
| 2005/0234518 A1 | 10/2005 | Heruth et al. |
| 2005/0240086 A1 | 10/2005 | Akay |
| 2005/0240242 A1 | 10/2005 | DiLorenzo |
| 2005/0245790 A1 | 11/2005 | Bergfalk et al. |
| 2005/0245988 A1 | 11/2005 | Miesel |
| 2006/0224191 A1 | 10/2006 | DiLorenzo |
| 2006/0293720 A1 | 12/2006 | DiLorenzo |
| 2007/0046408 A1 | 3/2007 | Shim |
| 2007/0073355 A1 | 3/2007 | DiLorenzo |
| 2007/0142862 A1 | 6/2007 | DiLorenzo |

FOREIGN PATENT DOCUMENTS

| | | |
|---|---|---|
| DE | 100 24 103 | 11/2001 |
| EP | 0 564 803 A1 | 10/1993 |
| EP | 0 849 715 B1 | 6/1998 |
| EP | 1 195 139 A1 | 4/2002 |
| EP | 1 291 036 A2 | 3/2003 |
| EP | 1 308 182 A2 | 5/2003 |
| EP | 1 437 159 A1 | 7/2004 |
| EP | 1 322 227 B1 | 12/2005 |
| GB | 2 330 912 A | 5/1999 |
| WO | WO 98/00197 | 1/1998 |
| WO | WO 99/13765 | 3/1999 |
| WO | WO 01/37930 | 5/2001 |
| WO | WO 02/28282 | 4/2002 |
| WO | WO 02/41771 | 5/2002 |
| WO | WO 02/087433 | 11/2002 |
| WO | WO 02/096512 | 12/2002 |
| WO | WO 02/100267 | 12/2002 |
| WO | WO 03/024325 | 3/2003 |
| WO | WO 03/051356 | 6/2003 |
| WO | WO 03/065891 | 8/2003 |
| WO | WO 2005/028029 | 3/2005 |
| WO | WO 2005/035050 | 4/2005 |

OTHER PUBLICATIONS

Response dated Dec. 14, 2009 for U.S. Appl. No. 11/081,857 (8 pgs.).
Advisory Action dated Jan. 12, 2010 for U.S. Appl. No. 11/081,857 (3 pgs.).
Office Action dated Nov. 6, 2008 for U.S. Appl. No. 11/081,857 (8 pgs.).
Response dated Jan. 6, 2009 for U.S. Appl. No. 11/081,857 (6 pgs.).
Office Action dated Oct. 16, 2007 for U.S. Appl. No. 10/826,925 (29 pgs.).
Response to Office Action dated Jan. 16, 2008 for U.S. Appl. No. 10/826,925 (20 pgs.).
Office Action dated Nov. 19, 2008 for U.S. Appl. No. 11/796,811 (7 pgs.).
Response dated Feb. 12, 2009 for U.S. Appl. No. 11/081,155 (7 pgs.).
Responsive Amendment dated Feb. 19, 2009 for U.S. Appl. No. 11/796,811 (15 pgs.).
Office Action dated Dec. 14, 2010 for U.S. Appl. No. 11/691,413, (6 pgs.).
Response dated Mar. 14, 2011 for U.S. Appl. No. 11/691,413, (2 pgs.).
Office Action dated Dec. 22, 2010 for U.S. Appl. No. 12/248,609, (7 pgs.).
Advisory Action dated Feb. 28, 2011 for U.S. Appl. No. 12/248,609, (3 pgs.).
Office Action dated Dec. 12, 2008 for U.S. Appl. No. 11/081,811 (12 pgs.).
Responsive Amendment dated Mar. 12, 2009 for U.S. Appl. No. 11/081,811 (13 pgs.).
Notice of Appeal and Pre-Appeal Brief Request for Review dated Mar. 22, 2011 for U.S. Appl. No. 12/248,609, (6 pgs.).
Office Action dated Dec. 21, 2009 for U.S. Appl. No. 11/691,405 (11 pgs.).
Responsive Amendment dated Mar. 22, 2010 for U.S. Appl. No. 11/691,405 (18 pgs.).
Office Action dated Jan. 12, 2010 for U.S. Appl. No. 11/691,411 (8 pgs.).
Responsive Amendment dated Apr. 12, 2010 for U.S. Appl. No. 11/691,411 (12 pgs.).
Office Action dated Feb. 17, 2011 for U.S. Appl. No. 11/691,405, (9 pgs.).
Responsive Amendment dated May 17, 2011 for U.S. Appl. No. 11/691,405, (14 pgs.).
Office Action dated Mar. 12, 2010 for U.S. Appl. No. 11/691,413 (7 pgs.).
Office Action dated May 20, 2010 for U.S. Appl. No. 12/248,622 (6 pgs.).
Responsive Amendment dated Jun. 9, 2010 for U.S. Appl. No. 11/691,413 (16 pgs.).
Office Action dated May 5, 2008 for U.S. Appl. No. 10/826,925 (12 pgs.).
Office Action dated May 30, 2008 for U.S. Appl. No. 11/081,811 (13 pgs.).
Office Action dated Apr. 23, 2008 for U.S. Appl. No. 11/796,811 (6 pgs.).
Office Action dated May 6, 2008 for U.S. Appl. No. 10/825,955 (13 pgs.).
Response to Office Action dated Jul. 2, 2008 for U.S. Appl. No. 10/825,955 (13 pgs.).
Office Action dated May 9, 2008 for U.S. Appl. No. 11/081,857 (10 pgs.).
Office Action dated Apr. 4, 2008 for U.S. Appl. No. 11/081,155 (9 pgs.).
van Dam et al., "Measuring physical activity in patients after surgery for a malignant tumour in the leg," The Journal of Bone & Joint Surgery, vol. 83-B, No. 7, pp. 1015-1019 (Sep. 2001).
Office Action dated Apr. 22, 2010 for U.S. Appl. No. 11/691,423 (8 pgs.).
Responsive Amendment dated Jul. 22, 2010 for U.S. Appl. No. 11/691,423 (15 pgs.).
Office Action dated May 6, 2010 for U.S. Appl. No. 12/017,918 (11 pgs.).
Office Action dated Apr. 28, 2010 for U.S. Appl. No. 11/081,811 (18 pgs.).
Office Action dated May 19, 2010 for U.S. Appl. No. 11/691,405 (12 pgs.).
Request for Continued Examination and Amendment dated Jul. 28, 2010 for U.S. Appl. No. 11/081,811 (19 pgs.).
Responsive Amendment dated Aug. 5, 2010 for U.S. Appl. No. 12/017,918 (16 pgs.).
Responsive Amendment dated Aug. 5, 2010 for U.S. Appl. No. 12/248,622 (10 pgs.).
Amzica, "Physiology of Sleep and Wakefulness as it Relates to the Physiology of Epilepsy," Journal of Clinical Neurophysiology, American Clinical Neurophysiology Society, 19(6), pp. 488-503, (2002).
Dinner, "Effect of Sleep on Epilepsy," Journal of Clinical Neurophysiology, American Clinical Neurophysiology Society, 19(6), pp. 504-513, (2002).
Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, (2002).
Mendez et al. "Interactions Between Sleep and Epilepsy," Journal of Clinical Neurophysiology, American Clinical Neurophysiology Society, 18(2), pp. 106-127, (2001).
"MiniMitter® Physiological and Behavioral Monitoring for Humans and Animals," http://www.minimitter.com/Products/Actiwatch, 3 pgs. Feb. 20, 2006.
"IBM & Citzen Watch develop Linux-based 'WatchPad'," 5 pgs., http://www.linuxdevices.com/news/NS6580187845.html, Feb. 20, 2006.
"Design Competition: Runners-Up for the Best Three Designs," EPN, vol. 26, No. 1, 1 pg., (2002).
"Watch," Wikipedia, the free encyclopedia, 6 pgs., http://en.wikipedia.org/wiki/Watch, Feb. 20, 2006.
Kassam, "2005 EDP Topic 'MK4': Tremor Data-Logger for Parkinson's Disease Patients," http://www.ee.ryerson.ca/~courses/edp2005/MK4.html, 3 pgs., Feb. 20, 2006.
Tuisku, "Motor Activity Measured by Actometry in Neuropsychiatric Disorders," Department of Psychiatry, University of Helsinski, Helsinki, Finland, 115 pgs. (2002).
Smith et al., "Presleep Cognitions in Patients with Insomnia Secondary to Chronic Pain," Journal of Behavioral Medicine, vol. 24, No. 1, pp. 93-114, (2001).
Smith et al. "How do sleep disturbance and chronic pain inter-relate? Insights from the longitudinal and cognitive-behavioral clinical trials literature," Sleep Medicine Reviews, YSMRV 286, pp. 1-14, (2003).
Goodrich et al., "The Prediction of Pain Using Measures of Sleep Quality," Pain Digest, 8:23-25, (1998).
"Analysis of heart rate dynamics by methods derived from nonlinear mathematics: Clinical applicability and prognostic significance" http:/herkules.oulu.fi.isbn9514250133/html, 4 pgs., (2004).
Kerr et al., "Analysis of the sit-stand-sit movement cycle in normal subjects," Clinical Biomechanics, vol. 12, No. 4, pp. 236-245, (1997).
Aminian et al. "Physical Activity Monitoring Based on Accelerometry: Validation and Comparison with Video Observation," Medical & Biological Engineering & Computing, vol. 37, No. 2, pp. 304-308 (1999).
Medcare—A Global Leader in Sleep Diagnostics, Embletta Recording System, http://www.medcare.com/products/diagnostic/embletta/, 2 pgs. Jan. 31, 2005.
Medcare—A Global Leader in Sleep Diagnostics, Somnologica for Embletta, http://www.medcare.com/products/diagnostic/embletta/SomnoEmbletta/index.asp, 1 pg. Jan. 31, 2005.
MAP Medizin—Technologie GmbH, Poly-MESAM®, http://195.244.124.130/map/de/eng/map_med.nsf/smsall/70564A3FCBE4188AC1256EF4.., 4 pgs. Jan. 31, 2005.
Merlin, http://www.aha.ru/~pir/english/merlin/, 4 pgs. Jan. 31, 2005.
Sleep Solutions—PR Newswire: Sleep Solutions Introduces NovaSom™ QSG™ for PSG.., http://www.sleep-solutions.com/press_room/novasom.htm, 2 pgs. Jan. 31, 2005.
Itamar Medical Information, http://itamar-medical.com/content.asp?id-id=31, 2 pgs. Jan. 31, 2005.

Criticare System Inc.,—504DX Portable Pulse Oximeter, http://www.csiusa.com/504dx.html, 4 pgs. Jan. 31, 2005.
Snap® Laboratories, Product Fact Sheet, http://www.snaplab.com/mp_fact.htm, 2 pgs. Jan. 31, 2005.
Sleep Strip & Bite Strip, http://ww.quietsleep.com/snoringapnea/sleepstrip.htm, 8 pgs. Jan. 31, 2005.
"Bitestrip Flier," downloaded from Internet Archive of www.quietsleep.com dated Jan. 29, 2005 http://web.archive.org/web/20041124080003/www.quietsleep.com/pdf/Bitestrip+Flier.pdf.
"Bilateral Comparisons of the BiteStrip Bruxism Device and Masseter EMG Bruxism Events" downloaded from Internet Archive of www.quietsleep.com dated Jan. 29, 2005 http://web.archive.org/web/20041124075114/www.quietsleep.com/pdf/Bilateral+Comparisons.pdf.
"The BiteStrip: A Novel Screener for Sleep Bruxism," downloaded from Internet Archive of www.quietsleep.com dated Jan. 29, 2005 http://web.archive.org/web/20041124072922/www.quietsleep.com/pdf/BiteStrip-+Novel+Screener.pdf.
Office Action dated Jul. 5, 2006 for U.S. Appl. No. 10/825,953, filed Apr. 15, 2004, (11 pgs.).
Responsive Amendment dated Oct. 5, 2006 for U.S. Appl. No. 10/825,953, filed Apr. 15, 2004 (17 pgs.).
Office Action dated Dec. 28, 2006 for U.S. Appl. No. 10/825,953, filed Apr. 15, 2004, (9 pgs.).
Response dated Feb. 28, 2007 for U.S. Appl. No. 10/825,953, filed Apr. 15, 2004 (7 pgs.).
Office Action dated Apr. 3, 2007 for U.S. Appl. No. 10/825,953, filed Apr. 15, 2004, (8 pgs.).
Responsive Amendment dated Jun. 28, 2007 for U.S. Appl. No. 10/825,953, filed Apr. 15, 2004 (19 pgs.).
Office Action dated Jul. 3, 2007 for U.S. Appl. No. 10/826,925, filed Apr. 15, 2004, (22 pgs.).
Office Action dated Mar. 11, 2009 for U.S. Appl. No. 10/826,925 (25 pgs.).
Responsive Amendment dated Aug. 11, 2009 for U.S. Appl. No. 10/826,925 (12 pgs.).
Office Action dated May 29, 2009 for U.S. Appl. No. 11/081,811 (13 pgs.).
Office Action dated Apr. 9, 2009 for U.S. Appl. No. 11/081,857 (12 pgs.).
Responsive Amendment dated Aug. 5, 2009 for U.S. Appl. No. 11/081,857 (12 pgs.).
Request for Continued Examination and Amendment dated Aug. 19, 2010 for U.S. Appl. No. 11/691,405 (17 pgs.).
Responsive Amendment dated Aug. 4, 2008 for U.S. Appl. No. 11/081,155 (12 pgs.).
Responsive Amendment dated Aug. 7, 2008 for U.S. Appl. No. 11/081,857 (13 pgs.).
Response dated Aug. 22, 2008 for U.S. Appl. No. 10/826,925 (7 pgs.).
Responsive Amendment dated Aug. 22, 2008 for U.S. Appl. No. 11/796,811 (13 pgs.).
Responsive Amendment dated Aug. 29, 2008 for U.S. Appl. No. 11/081,811 (13 pgs.).
Office Action dated May 10, 2011 for U.S. Appl. No. 12/248,622, (6 pgs.).
Responsive Amendment dated Aug. 10, 2011 for U.S. Appl. No. 12/248,622, (10 pgs.).
Office Action dated May 10, 2011 for U.S. Appl. No. 12/248,609, (7 pgs.).
Responsive Amendment dated Aug. 10, 2011 for U.S. Appl. No. 12/248,609, (11 pgs.).
Advisory Action dated Oct. 12, 2010 for U.S. Appl. No. 12/351,414, (3 pgs.).
Office Action dated Aug. 2, 2010 for U.S. Appl. No. 12/351,414, (21 pgs.).
Response dated Oct. 1, 2010 for U.S. Appl. No. 12/351,414, (10 pgs.).
Office Action dated Jul. 14, 2010 for U.S. Appl. No. 11/691,413, (7 pgs.).
Response dated Sep. 14, 2010 for U.S. Appl. No. 11/691,413, (7 pgs.).
Office Action dated Aug. 5, 2010 for U.S. Appl. No. 12/248,609, (8 pgs.).
Office Action dated Aug. 4, 2009 for U.S. Appl. No. 11/413,619 (9 pgs.).
Response dated Nov. 4, 2009 for U.S. Appl. No. 11/413,619 (7 pgs.).
Responsive Amendment dated Nov. 4, 2010 for U.S. Appl. No. 12/248,609, (10 pgs.).
Office Action dated Sep. 29, 2010 for U.S. Appl. No. 12/248,622, (7 pgs.).
Response dated Nov. 18, 2010 for U.S. Appl. No. 12/248,622, (10 pgs.).
Final Office Action dated Oct. 20, 2011 for U.S. Appl. No. 12/248,622, (8 pgs.).
Response dated Dec. 20, 2011 for U.S. Appl. No. 12/248,622, (5 pgs.).
Final Office Action dated Oct. 20, 2011 for U.S. Appl. No. 12/248,609, (8 pgs.).
Response dated Dec. 20, 2011 for U.S. Appl. No. 12/248,609, (7 pgs.).
Office Action dated Nov. 9, 2012 for U.S. Appl. No. 11/691,376, (30 pgs.).
Responsive Amendment dated Feb. 8, 2012 for U.S. Appl. No. 11/691,376, (17 pgs.).
Cicolin et al., "Effects of deep brain stimulation of the subthalamic nucleus on sleep architecture in parkinsonian patients," Sleep Medicine, vol. 5, Issue 2, pp. 207-210, Mar. 2004.
Oerlemans et al., "The prevalence of sleep disorders in patients with Parkinson's disease. A self-reported, community-based survey," Sleep Medicine, vol. 3, Issue 2, pp. 147-149, Mar. 2002.
Antonini et al., "Deep brain stimulation and its effect on sleep in Parkinson's disease," Sleep Medicine, vol. 5, Issue 2, pp. 211-214, Mar. 2004.
Final Office Action dated Mar. 19, 2012 for U.S. Appl. No. 11/691,376, (37 pgs.).
Office Action dated May 3, 2012 for U.S. Appl. No. 12/544,727, (10 pgs.).
Final Office Action dated Mar. 1, 2012 for U.S. Appl. No. 11/591,286, (31 pgs.).
Responsive Amendment dated May 1, 2012 for U.S. Appl. No. 11/591,286, (16 pgs.).
Decision on Appeal dated Mar. 14, 2012 for U.S. Appl. No. 11/081,857, (7 pgs.).
Responsive Amendment dated Jun. 15, 2012 for U.S. Appl. No. 11/691,376, (17 pgs.).
Responsive Amendment dated Jul. 31, 2012 for U.S. Appl. No. 12/544,727, (12 pgs.).
Office Action dated Jul. 5, 2012 for U.S. Appl. No. 11/591,286, (34 pgs.).

| PARAMETER SET | PARAMETERS | SLEEP EFFICIENCY | SLEEP LATENCY | % OF TIME ACTIVE |
|---|---|---|---|---|
| 1 | PA = 5.5V<br>PW = 210ms<br>PR = 90Hz | 85% | 20 min. | 75%<br>(15% HIGH) |
| 2 | PA = 5V<br>PW = 190ms<br>PR = 95Hz | 75% | 25 min. | 60%<br>(5% HIGH) |
| ••• | | | | |
| N | PA = 4.6V<br>PW = 215ms<br>PR = 80Hz | 70% | 38 min. | 55%<br>(8% HIGH) |

FIG. 10

COLLECTING ACTIVITY AND SLEEP QUALITY INFORMATION VIA A MEDICAL DEVICE

This application is a continuation-in-part of U.S. application Ser. No. 11/081,857, filed Mar. 16, 2005 and published as U.S. patent application publication no. 2005/0234518, now abandoned which is a continuation-in-part of U.S. application Ser. No. 10/825,955, filed Apr. 15, 2004 and issued as U.S. Pat. No. 7,491,181, which claims the benefit of U.S. provisional application No. 60/553,785, filed Mar. 16, 2004. This application also claims the benefit of U.S. Provisional Application No. 60/785,662, filed Mar. 24, 2006. The entire content of each of these applications is incorporated herein by reference.

TECHNICAL FIELD

The invention relates to medical devices and, more particularly, to medical devices that monitor physiological parameters.

BACKGROUND

In some cases, an ailment may affect the quality of a patient's sleep and/or affect the patient's activity level. For example, chronic pain may cause a patient to have difficulty falling asleep, disturb the patient's sleep, e.g., cause the patient to wake, and prevent the patient from achieving deeper sleep states, such as one or more of the nonrapid eye movement (NREM) sleep states. Chronic pain may also cause a patient to avoid particular activities, or activity in general, where such activities increase the pain experienced by the patient.

Other ailments that may negatively affect patient sleep quality and patient activity level include movement disorders, such as tremor, Parkinson's disease, multiple sclerosis, epilepsy, or spasticity. Such movement disorders may result in irregular movement or activity, as well as a generally decreased level of activity. Further, the uncontrolled movements associated with such movement disorders may cause a patient to have difficulty falling asleep, disturb the patient's sleep, or cause the patient to have difficulty achieving deeper sleep states.

Psychological disorders, such as depression, mania, bipolar disorder, or obsessive-compulsive disorder, and other disorders including sleep apnea, congestive heart failure, gastrointestinal disorders and incontinence, may also similar affect the ability of a patient to sleep, or at least experience quality sleep. In the case of depression, a patient may "sleep" for long periods of the day, but the sleep is not restful, e.g., includes excessive disturbances and does not include deeper, more restful sleep states. Further, during the day, psychological disorders may also affect the general activity level of a patient. For example, patients with depression may spend a significant majority of their time in bed or otherwise prone. Movement disorders and psychological disorders are examples of neurological disorders.

Congestive heart failure is another example of a disorder that affects both sleep quality and activity. Patients with congestive heart failure may lack the stamina for activity during the day, and may have difficulty breathing at night, which may affect the quality of their sleep. In some cases, the above-identified ailments may be treated via an implantable medical device (IMD), such as an implantable stimulator or drug delivery device.

Further, in some cases, poor sleep quality may increase the symptoms experienced by a patient due to an ailment. For example, poor sleep quality has been linked to increased pain, movement disorder and psychological disorder symptoms in chronic pain patients. The link between poor sleep quality and increased symptoms is not limited to ailments that negatively impact sleep quality, such as those listed above. Nonetheless, the condition of a patient with such an ailment may progressively worsen when symptoms disturb sleep quality, which in turn increases the frequency and/or intensity of symptoms. The increased symptoms may, in turn, limit patient activity during the day, and further disturb sleep quality.

SUMMARY

In general, the invention is directed to techniques for collecting information that relates to patient activity and the quality of patient sleep via a medical device, such as an implantable medical device (IMD). The medical device, or another device, determines whether to collect activity or sleep quality information by determining whether the patient is attempting to sleep. Activity and sleep quality information collected by the device may be presented to a user, such as a clinician, and used to, for example, evaluate the effectiveness of a therapy delivered to the patient by the medical device. For example, the activity and sleep quality information may be associated with different therapy parameter sets used by the medical device to deliver therapy to the patient, permitting a user to evaluate relative efficacy of the therapy parameter sets.

The device may determine that the patient is attempting to sleep in a variety of ways. For example, the device may receive an indication from the patient that the patient is trying to fall asleep, e.g., via a patient programming device in embodiments in which the medical device determines whether the patient is attempting to sleep and is an implantable medical device. In other embodiments, the device may monitor the activity level of the patient, and identify the time that the patient is attempting to sleep by determining whether the patient has remained inactive for a threshold period of time and identifying the time at which the patient became inactive. In still other embodiments, the device may monitor patient posture, and identify the time when the patient is recumbent, e.g., lying down, as the time when the patient is attempting to fall asleep. In these embodiments, the device may also monitor patient activity, and confirm that the patient is attempting to sleep based on the patient's activity level.

As another example, the device may determine the time at which the patient begins attempting to fall asleep based on the level of melatonin within one or more bodily fluids, such as the patient's blood, cerebrospinal fluid (CSF), or interstitial fluid. The device may also determine a melatonin level based on metabolites of melatonin located in the saliva or urine of the patient. Melatonin is a hormone secreted by the pineal gland into the bloodstream and the CSF as a function of exposure of the optic nerve to light, which synchronizes the patient's circadian rhythm. In particular, increased levels of melatonin during evening hours may cause physiological changes in the patient, which, in turn, may cause the patient to attempt to fall asleep. The device may, for example, detect an increase in the level of melatonin, and estimate the time that the patient will attempt to fall asleep based on the detection.

When the device determines that the patient is attempting to sleep, the device may determine values for one or more metrics that indicate the quality of a patient's sleep based on at least one monitored physiological parameter of the patient. Example physiological parameters that the device may monitor to determine sleep quality metric values include activity level, posture, heart rate, electrocardiogram (ECG) morphology, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, brain electrical activity, electroencephalogram (EEG) morphology, eye motion, and galvanic skin response. In order to monitor one or more of these parameters, the device may include, or be coupled to, one or more sensors, each of which generates a signal as a function of one or more of these physiological parameters. The device may determine a value of one or more sleep quality metrics based on the monitored physiological parameters, and/or the variability of one or more of the monitored physiological parameters.

Sleep efficiency and sleep latency are example sleep quality metrics for which a device may determine values. Sleep efficiency may be measured as the percentage of time while the patient is attempting to sleep that the patient is actually asleep, or actually within one of the different sleep states. Sleep latency may be measured as the amount of time between a first time when the patient begins attempting to fall asleep and a second time when the patient falls asleep, and thereby indicates how long a patient requires to fall asleep.

The time when the patient begins attempting to fall asleep may be determined in any of the variety of ways identified above. The time at which the patient has fallen asleep may be determined based on any one or more of the other physiological parameters that may be monitored by the medical device as indicated above. For example, a discernable change, e.g., a decrease, in one or more physiological parameters, or the variability of one or more physiological parameters, may indicate that the patient has fallen asleep. In some embodiments, the device determines a sleep probability metric value based on a value of a physiological parameter. In such embodiments, the device compares the sleep probability metric value to a threshold to identify when the patient has fallen asleep. In some embodiments, the medical device determines a plurality of sleep probability metric values based on a value of each of a plurality of physiological parameters, averages or otherwise combines the plurality of sleep probability metric values to provide an overall sleep probability metric value, and compares the overall sleep probability metric value to a threshold to identify the time that the patient falls asleep.

Other sleep quality metrics that the device may determine include total time sleeping per day, the amount or percentage of time sleeping during nighttime or daytime hours per day, and the number of apnea and/or arousal events per night. In some embodiments, the device may determine which sleep state the patient is in, e.g., rapid eye movement (REM), or one of the nonrapid eye movement (NREM) states (S1, S2, S3, S4) based on monitored physiological parameters, and the amount of time per day spent in these various sleep states may be determined by the medical device as a sleep quality metric. Because they provide the most "refreshing" type of sleep, the amount of time spent in one or both of the S3 and S4 sleep states, in particular, may be determined as a sleep quality metric. In some embodiments, the device may determine average or median values of one or more sleep quality metrics over greater periods of time, e.g., a week or a month, as the value of the sleep quality metric. Further, in embodiments in which values for a plurality of the sleep quality metrics are determined, the device may determine a value for an overall sleep quality metric based on the values for the plurality of individual sleep quality metrics.

When the device determines that the patient is not attempting to sleep, the device periodically determines activity levels of the patient. For example, the device may monitor a signal generated by an accelerometer, a bonded piezoelectric crystal, a mercury switch, or a gyro. In some embodiments, the device may monitor a signal that indicates a physiological parameter of the patient, which in turn varies as a function of patient activity. For example, the device may monitor a signal that indicates the heart rate, ECG morphology, respiration rate, respiratory volume, core temperature, subcutaneous temperature, or muscular activity level of the patient.

The device may periodically determine an activity level of the patient based on the one or more signals. In some embodiments, the device periodically determines a number of activity counts based on the one or more signals, and the number of activity counts is stored as the activity level. The number of activity counts may be a number of threshold crossings by a signal generated by an accelerometer or piezoelectric crystal during a sample period, or a number of switch contacts indicated by the signal generated by a mercury switch during a sample period.

In some embodiments, the device may periodically determine a heart rate, value of an ECG morphological feature, respiration rate, respiratory volume, and/or muscular activity level of the patient based on one or more signals. The determined values of these parameters may be mean or median values. The device may compare a determined value of such a physiological parameter to one or more thresholds to determine a number of activity counts, which may be stored as a determined activity level. In other embodiments, the device may store the determined physiological parameter value as a determined activity level.

The use of activity counts, however, may allow the device to determine an activity level based on a plurality of signals. For example, the device may determine a first number of activity counts based on a sample of an accelerometer signal and a second number of activity counts based on a heart rate determined at the time the accelerometer signal was sampled. The device may determine an activity level by calculating the sum or average, which may be a weighted sum or average, of first and second activity counts.

The device may determine a value of one or more activity metrics based on determined activity levels. An activity metric value may be, for example, a mean or median activity level, such as an average number of activity counts per unit time. In other embodiments, an activity metric value may be chosen from a predetermined scale of activity metric values based on comparison of a mean or median activity level to one or more threshold values. The scale may be numeric, such as activity metric values from 1-10, or qualitative, such as low, medium or high activity.

In some embodiments, a number of collected activity levels are compared with one or more thresholds, and percentages of time above and/or below the thresholds are determined as one or more activity metric values. In other embodiments, a number of collected activity levels are compared with one or more thresholds, and an average length of time that consecutively determined activity levels remain above the threshold is determined as an activity metric value.

In some embodiments, the device that collects sleep quality and activity information is a medical device delivers a therapy to the patient. At any given time, the medical device delivers the therapy according to a current set of therapy parameters. For example, in embodiments in which the medical device is a neurostimulator, a therapy parameter set may include a pulse amplitude, a pulse width, a pulse rate, a duty cycle, and an indication of active electrodes. Different therapy parameter sets may be selected, e.g., by the patient via a programming device or a the medical device according to a schedule, and parameters of one or more therapy parameter sets may be adjusted by the patient to create new therapy parameter sets. In other words, over time, the medical device delivers the therapy according to a plurality of therapy parameter sets.

When the medical device determines a sleep quality metric value or an activity level, the medical device may identify the current therapy parameter set when the value or level is determined, and may associate that value or level with the therapy parameter set. For each available therapy parameter set, the medical device may store a representative value of each of one or more sleep quality metrics in a memory with an indication of the therapy parameter set with which that representative value is associated. A representative value of sleep quality metric for a therapy parameter set may be the mean or median of collected sleep quality metric values that have been associated with that therapy parameter set. For each available therapy parameter set, the medical device may also store one or more associated activity metric values that are determined based on activity levels associated with that therapy parameter set.

A programming device according to the invention may be capable of wireless communication with the medical device, and may receive from the medical device information identifying the therapy parameter set, representative sleep quality metric values associated with the plurality of therapy parameter sets, and activity metric values associated with the therapy parameter sets. The programming device may display a list of the therapy parameter sets, which may be ordered according to any of the associated representative sleep quality metric values or activity metric values. A user may select the metric by which the list is ordered. Such a list may be used by a clinician to, for example, identify effective or ineffective therapy parameter sets.

In some embodiments, the medical device does not determine whether the patient is attempting to sleep, determine values for sleep quality metrics, determine activity metric values, and/or periodically determine activity levels. Instead, in some embodiments, a computing device, such as a programming device performs one or more of these functions. For example, a programming device may be used to program a medical device, and also receive physiological parameter values, activity levels, and/or samples of an activity signal from the medical device, and determine activity metric values and sleep quality metric values based on the information received from the medical device using any of the techniques described herein with reference to a medical device.

In some embodiments, the medical device may associate recorded physiological parameter values, signal samples, and/or activity levels with a current therapy parameter set, and may provide information identifying a plurality of therapy parameter sets and collected information associated with the therapy parameter sets to a programming device or other computing device. In such embodiments, the programming device may determine representative sleep quality metric values and activity metric values associated with the various therapy parameter sets using any of techniques described herein with reference to a medical device. The programming device may receive such information from the medical device in real time, or may interrogate the medical device for information recorded by the medical device over a period of time.

In other embodiments, a system according to the invention does not include a programming device or other computing device. For example, an external medical device according to the invention may include a display, collect sleep quality and activity information as described herein, and display sleep quality and activity information to a user via the display.

In one embodiment, the invention is directed to a method in which a plurality of physiological parameters of a patient are monitored. The plurality of physiological parameters includes at least one physiological parameter indicative of patient physical activity. The method includes a determination of when the patient is attempting to sleep. Values of at least one metric that is indicative of sleep quality are determined based on at least one of the physiological parameters and a determination that the patient is attempting to sleep. The method further includes periodically determining values of an activity metric based on at least one of the physiological parameters and a determination that the patient is not attempting to sleep, and associating each of the sleep quality and activity metric values with a therapy parameter set currently used by a medical device to deliver at least one of a movement disorder therapy, psychological disorder therapy, or deep brain stimulation to the patient when the metric value was determined.

In another embodiment, the invention is directed to a medical system including a device and a processor. The device monitors a plurality of physiological parameters of a patient, and the plurality of physiological parameters includes at least one physiological parameter indicative of patient physical activity. The processor determines when the patient is attempting to sleep, determines values of at least one metric that is indicative of sleep quality based on at least one of the physiological parameters and a determination that the patient is attempting to sleep, and periodically determines a value of an activity metric based on at least one of the physiological parameters and a determination that the patient is not attempting to sleep, and associates each of the sleep quality and activity metric values with a therapy parameter set currently used by the medical device to deliver the therapy when the metric value was determined.

In another embodiment, the invention is directed to a computer-readable medium having instructions that cause a processor to monitor a plurality of physiological parameters of a patient, wherein the plurality of physiological parameters includes at least one parameter indicative of patient physical activity, determine when the patient is attempting to sleep, and determine values of at least one metric that is indicative of sleep quality based on at least one of the physiological parameters and a determination that the patient is attempting to sleep. The computer-readable medium also includes instructions that cause the processor to periodically determine values of an activity metric based on at least one of the physiological parameters and a determination that the patient is not attempting to sleep and associate each of the sleep quality and activity metric values a therapy parameter set currently used by a medical device to deliver at least one of a movement disorder therapy, psychological disorder therapy, or deep brain stimulation to the patient when the metric value is determined.

The invention may be capable of providing one or more advantages. For example, by providing information related to patient activity and the quality of a patient's sleep to a clinician and/or the patient, a system according to the invention can improve the course of treatment of an ailment of the patient, such as chronic pain, a movement disorder, a psychological disorder, or congestive heart failure. For example, using activity and sleep quality information provided by the system, the clinician could evaluate a plurality of therapy parameter sets to identify those which are, or are not, efficacious.

The details of one or more embodiments of the invention are set forth in the accompanying drawings and the descrip-

BRIEF DESCRIPTION OF DRAWINGS

FIG. 10 illustrates an example list of therapy parameter sets and associated sleep quality information and activity information that may be presented by a clinician programmer.

DETAILED DESCRIPTION

Figure 1A:
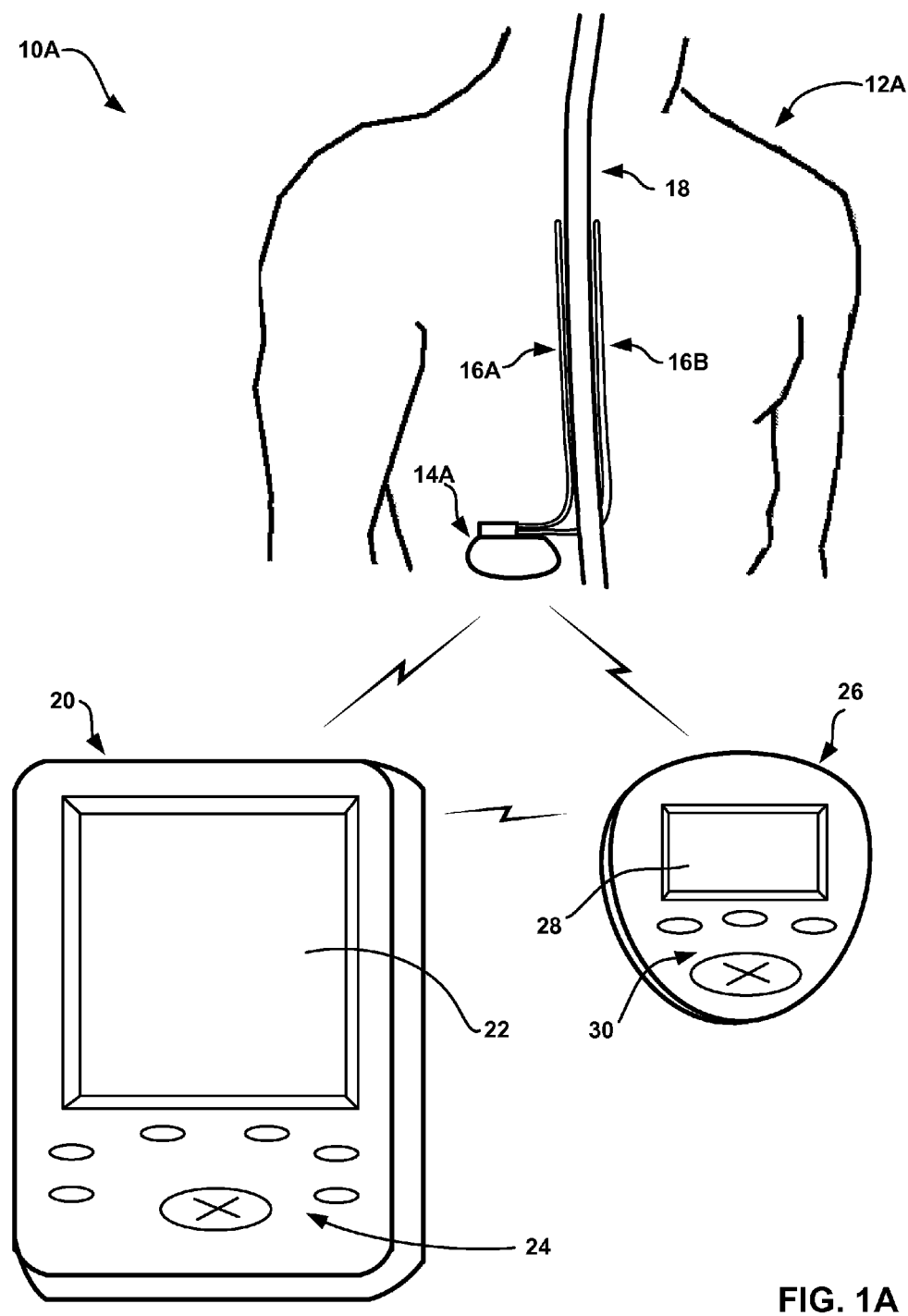
FIGS. 1A and 1B are conceptual diagrams illustrating example systems that include an implantable medical device that collects sleep quality information and activity information according to the invention.
Figure 1B:
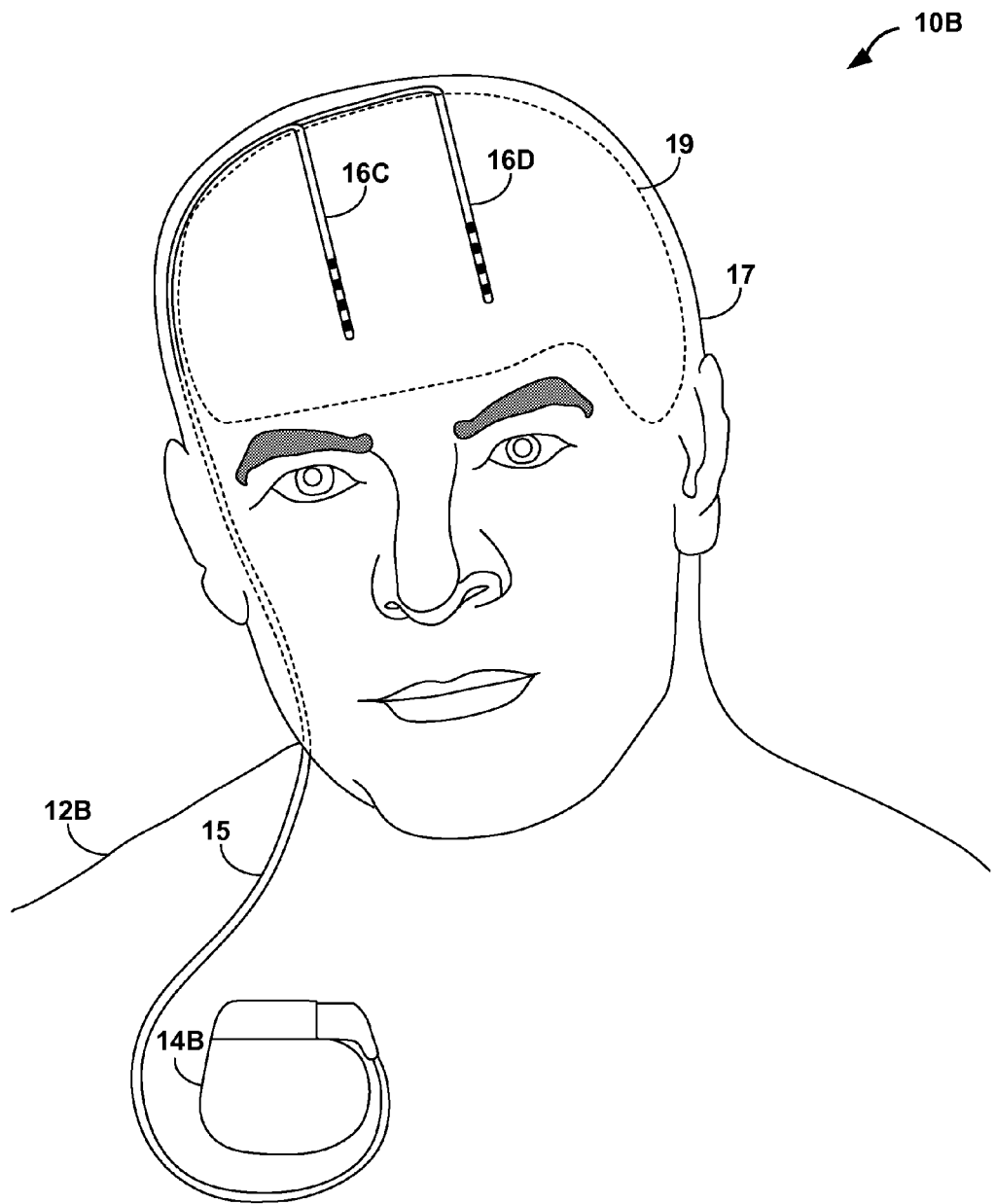

FIGS. 1A and 1B are conceptual diagrams illustrating example systems 10A and 10B (collectively "systems 10") that respectively include an implantable medical device (IMD) 14A or 14B (collectively "IMDs 14") that collect information relating to the quality of sleep experienced by a respective one of patients 12A and 12B (collectively "patients 12") and the activity of patients 12 according to the invention. Sleep quality information and activity information may be collected by IMDs 14 are provided to one or more users, such as a clinician or the patient. Using the sleep quality information and activity information collected by IMDs 14, a current course of therapy for one or more ailments of patient 12 may be evaluated, and an improved course of therapy for the ailment may be identified.

In the illustrated example systems 10, IMDs 14 take the form of implantable neurostimulators that deliver neurostimulation therapy in the form of electrical pulses to patients 12. However, the invention is not limited to implementation via implantable neurostimulators. For example, in some embodiments of the invention, an implantable pump or implantable cardiac rhythm management device, such as a pacemaker may collect sleep quality information and activity information. Further, the invention is not limited to implementation via an IMD. In other words, any implantable or external medical device may collect sleep quality and activity information according to the invention.

In the examples of FIGS. 1A and 1B, IMDs 14A and 14B deliver neurostimulation therapy to patients 12A and 12B via leads 16A and 16B, and leads 16C and 16D (collectively "leads 16"), respectively. Leads 16A and 16B may, as shown in FIG. 1A, be implanted proximate to the spinal cord 18 of patient 12A, and IMD 14A may deliver spinal cord stimulation (SCS) therapy to patient 12A in order to, for example, reduce pain experienced by patient 12A. However, the invention is not limited to the configuration of leads 16 shown in FIG. 1A or the delivery of SCS or other pain therapies.

For example, in another embodiment, illustrated in FIG. 1B, leads 16C and 16D may extend to brain 19 of patient 12B, e.g., through cranium 17 of patient. IMD 14B may deliver deep brain stimulation (DBS) or cortical stimulation therapy to patient 12 to treat any of a variety of non-respiratory neurological disorders, such as movement disorders or psychological disorders. In general, non-respiratory neurological disorders do not include respiratory disorders, such as sleep apnea. Example therapies may treat tremor, Parkinson's disease, spasticity, epilepsy, depression or obsessive-compulsive disorder. As illustrated in FIG. 1B, leads 16C and 16D may be coupled to IMD 14B via one or more lead extensions 15.

As further examples, one or more leads 16 may be implanted proximate to the pelvic nerves (not shown) or stomach (not shown), and an IMD 14 may deliver neurostimulation therapy to treat incontinence or gastroparesis. Additionally, leads 16 may be implanted on or within the heart to treat any of a variety of cardiac disorders, such as congestive heart failure or arrhythmia, or may be implanted proximate to any peripheral nerves to treat any of a variety of disorders, such as peripheral neuropathy or other types of chronic pain.

The illustrated numbers and locations of leads 16 are merely examples. Embodiments of the invention may include any number of lead implanted at any of a variety of locations within a patient. Furthermore, the illustrated number and location of IMDs 14 are merely examples. IMDs 14 may be located anywhere within patient according to various embodiments of the invention. For example, in some embodiments, an IMD 14 may be implanted on or within cranium 17 for delivery of therapy to brain 19, or other structure of the head of the patient 12.

IMDs 14 delivers therapy according to a set of therapy parameters, i.e., a set of values for a number of parameters that define the therapy delivered according to that therapy parameter set. In embodiments where IMDs 14 deliver neurostimulation therapy in the form of electrical pulses, the parameters for each therapy parameter set may include voltage or current pulse amplitudes, pulse widths, pulse rates, and the like. Further, each of leads 16 includes electrodes (not shown in FIGS. 1A and 1B), and a therapy parameter set may include information identifying which electrodes have been selected for delivery of pulses, and the polarities of the selected electrodes. In embodiments in which IMDs 14 deliver other types of therapies, therapy parameter sets may include other therapy parameters such as drug concentration and drug flow rate in the case of drug delivery therapy. Therapy parameter sets used by an IMD 14 may include a number of parameter sets programmed by a clinician (not shown), and parameter sets representing adjustments made by patient 12 to these preprogrammed sets.

Each of systems 10 may also include a clinician programmer 20 (illustrated as part of system 10A in FIG. 1A). A clinician (not shown) may use clinician programmer 20 to program therapy for patient 12A, e.g., specify a number of therapy parameter sets and provide the parameter sets to IMD 14A. The clinician may also use clinician programmer 20 to retrieve information collected by IMD 14A. The clinician may use clinician programmer 20 to communicate with IMD 14A both during initial programming of IMD 14A, and for collection of information and further programming during follow-up visits.

Clinician programmer 20 may, as shown in FIG. 1A, be a handheld computing device. Clinician programmer 20 includes a display 22, such as a LCD or LED display, to display information to a user. Clinician programmer 20 may also include a keypad 24, which may be used by a user to interact with clinician programmer 20. In some embodiments, display 22 may be a touch screen display, and a user may interact with clinician programmer 20 via display 22. A user may also interact with clinician programmer 20 using peripheral pointing devices, such as a stylus or mouse. Keypad 24 may take the form of an alphanumeric keypad or a reduced set of keys associated with particular functions.

Systems 10 may also includes a patient programmer 26 (illustrated as part of system 10A in FIG. 1A), which also may, as shown in FIG. 1A, be a handheld computing device. Patient 12 may use patient programmer 26 to control the delivery of therapy by IMD 14A. For example, using patient programmer 26, patient 12A may select a current therapy parameter set from among the therapy parameter sets preprogrammed by the clinician, or may adjust one or more parameters of a preprogrammed therapy parameter set to arrive at the current therapy parameter set.

Patient programmer 26 may include a display 28 and a keypad 30, to allow patient 12A to interact with patient programmer 26. In some embodiments, display 28 may be a touch screen display, and patient 12A may interact with patient programmer 26 via display 28. Patient 12A may also interact with patient programmer 26 using peripheral pointing devices, such as a stylus, mouse, or the like.

However, clinician and patient programmers 20, 26 are not limited to the hand-held computer embodiments illustrated in FIG. 1A. Programmers 20, 26 according to the invention may be any sort of computing device. For example, a programmer 20, 26 according to the invention may be a tablet-based computing device, a desktop computing device, or a workstation.

IMDs 14, clinician programmers 20 and patient programmers 26 may, as shown in FIG. 1A, communicate via wireless communication. Clinician programmer 20 and patient programmer 26 may, for example, communicate via wireless communication with IMD 14A using radio frequency (RF) or infrared telemetry techniques known in the art. Clinician programmer 20 and patient programmer 26 may communicate with each other using any of a variety of local wireless communication techniques, such as RF communication according to the 802.11 or Bluetooth specification sets, infrared communication according to the IRDA specification set, or other standard or proprietary telemetry protocols.

Clinician programmer 20 and patient programmer 26 need not communicate wirelessly, however. For example, programmers 20 and 26 may communicate via a wired connection, such as via a serial communication cable, or via exchange of removable media, such as magnetic or optical disks, or memory cards or sticks. Further, clinician programmer 20 may communicate with one or both of IMD 14 and patient programmer 26 via remote telemetry techniques known in the art, communicating via a local area network (LAN), wide area network (WAN), public switched telephone network (PSTN), or cellular telephone network, for example.

As mentioned above, an IMD 14 collects information that relates to the quality of sleep experienced by a patient 12 and the activity of the patient 12. In particular, as will be described in greater detail below, an IMD 14 determines whether a patient 12 is attempting to sleep, determines values for one or more sleep quality metrics when the patient 12 is attempting to sleep, and periodically determines activity levels of the patient 12 when the patient 12 is not attempting to sleep, i.e., is more likely to be active. In some embodiments, an IMD 14 determines values for one or more activity metrics based on the determined activity levels. An IMD 14 may include or be coupled to one or more sensors (not shown in FIGS. 1A and 1B), each of which generates a signal as a function of one or more of these physiological parameters, and may determine sleep quality metrics and activity levels based on the signals output by the sensors.

At any given time, as indicated above, an IMD 14 delivers the therapy according to a current set of therapy parameters. Different therapy parameter sets may be selected, e.g., by a patient 12 via patient programmer 26 or an IMD 14 according to a schedule, and parameters of one or more therapy parameter sets may be adjusted by a patient 12 via patient programmer 26 to create new therapy parameter sets. In other words, over time, an IMD 14 delivers the therapy according to a plurality of therapy parameter sets.

In some embodiments, as will be described in greater detail below, an IMD 14 identifies the therapy parameter set currently used to deliver therapy to a patient 12 when a value of a sleep quality metric or an activity level is determined, and may associate the determined values and levels with current therapy parameter sets. For each of the plurality of therapy parameter sets, an IMD 14 may store a representative value of each of one or more sleep quality metrics in a memory with an indication of the therapy parameter set with which that representative value is associated. A representative value of a sleep quality metric for a therapy parameter set may be the mean or median of collected sleep quality metric values that have been associated with that therapy parameter set. For each available therapy parameter set, an IMD 14 may also store one or more associated activity metric values that are determined based on activity levels associated with that therapy parameter set.

A programming or other computing device, such as clinician programmer 20, may receive information identifying the therapy parameter set, representative sleep quality metric values associated with the plurality of therapy parameter sets, and activity metric values associated with the therapy parameter sets from an IMD 14. Clinician programmer 20 may display a list of the therapy parameter sets, which may be ordered according to any of the associated representative sleep quality metric values or activity metric values. A clinician may select the metric by which the list is ordered. Such a list may be used by the clinician to, for example, identify effective or ineffective therapy parameter sets.

Figure 2A:
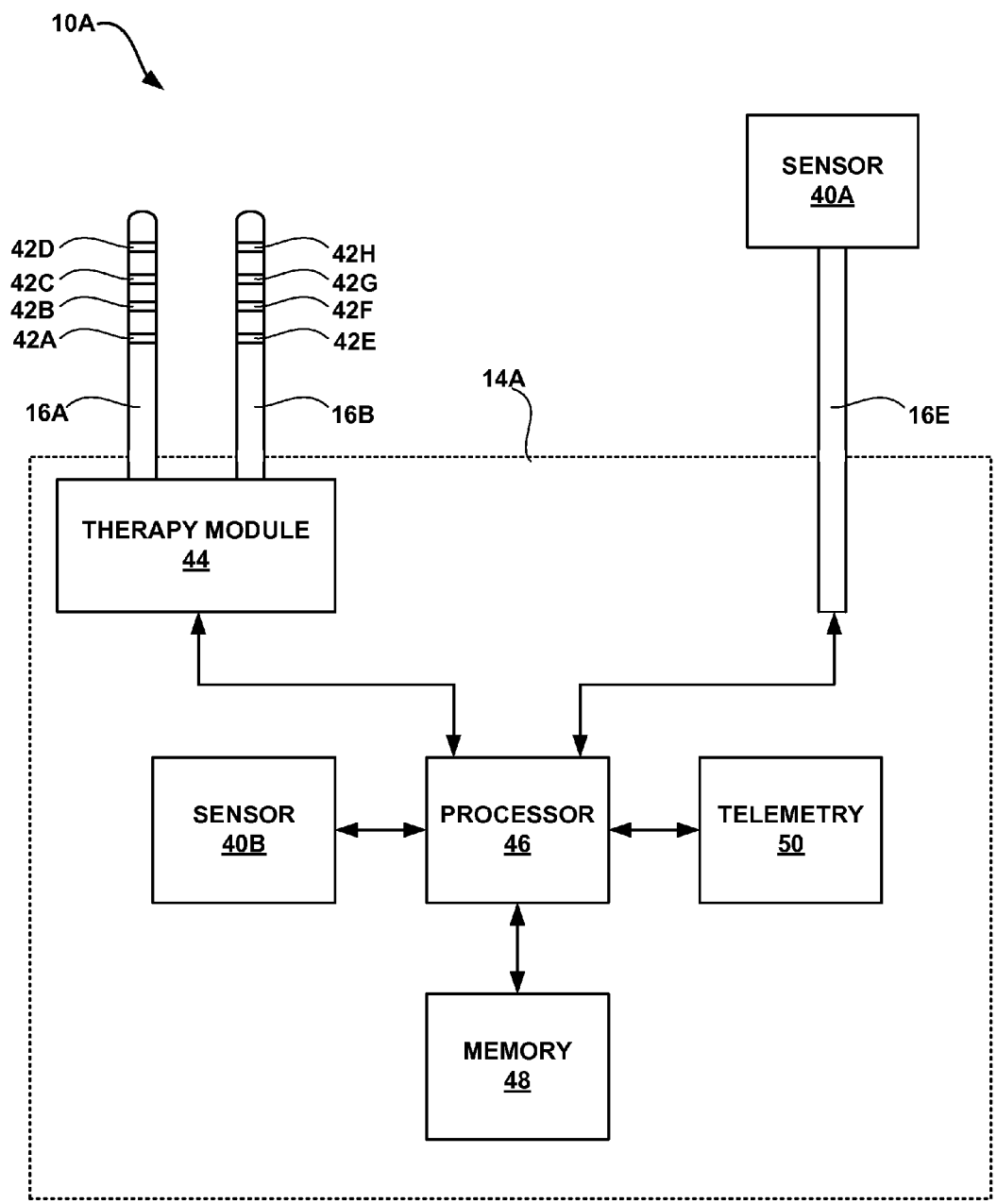
FIGS. 2A and 2B are block diagrams further illustrating the example systems and implantable medical devices of FIGS. 1A and 1B.
Figure 2B:
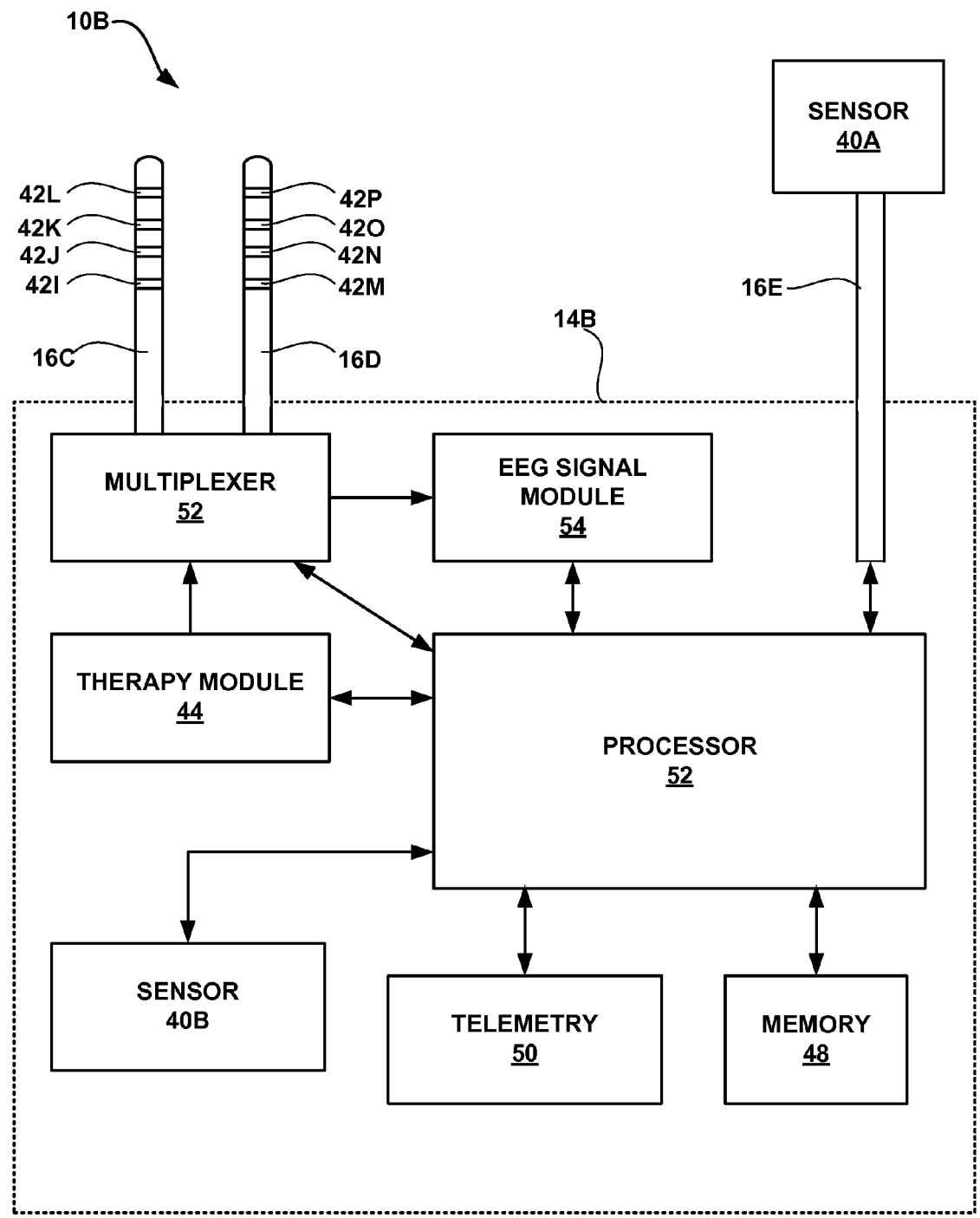

FIGS. 2A and 2B are block diagrams further illustrating systems 10A and 10B. In particular, FIG. 2A illustrates an example configuration of IMD 14A and leads 16A and 16B.

FIG. 2B illustrates an example configuration of IMD 14B and leads 16C and 16D. FIGS. 2A and 2B also illustrate sensors 40A and 40B (collectively "sensors 40") that generate signals as a function of one or more physiological parameters of patients 12. As will be described in greater detail below, IMDs 14 monitor at least some of the signals to determine values for one or more metrics that are indicative of sleep quality when the patient is attempting to sleep, and monitors at least some of the signals to determine activity levels of patient 12 when the patient is not attempting to sleep.

IMD 14A may deliver neurostimulation therapy via electrodes 42A-D of lead 16A and electrodes 42E-H of lead 16B, while IMD 14B delivers neurostimulation via electrodes 42I-L of lead 16C and electrodes 42 M-P of lead 16D (collectively "electrodes 42"). Electrodes 42 may be ring electrodes. The configuration, type and number of electrodes 42 illustrated in FIGS. 2A and 2B are merely exemplary. For example, leads 16 may each include eight electrodes 42, and the electrodes 42 need not be arranged linearly on each of leads 16.

In each of systems 10A and 10B, electrodes 42 are electrically coupled to a therapy delivery module 44 via leads 16. Therapy delivery module 44 may, for example, include an output pulse generator coupled to a power source such as a battery. Therapy delivery module 44 may deliver electrical pulses to a patient 12 via at least some of electrodes 42 under the control of a processor 46, which controls therapy delivery module 44 to deliver neurostimulation therapy according to a current therapy parameter set. However, the invention is not limited to implantable neurostimulator embodiments or even to IMDs that deliver electrical stimulation. For example, in some embodiments, a therapy delivery module 44 of an IMD may include a pump, circuitry to control the pump, and a reservoir to store a therapeutic agent for delivery via the pump.

Processor 46 may include a microprocessor, a controller, a digital signal processor (DSP), an application specific integrated circuit (ASIC), a field-programmable gate array (FPGA), discrete logic circuitry, or the like. Memory 48 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. In some embodiments, memory 48 stores program instructions that, when executed by processor 46, cause IMD 14 and processor 46 to perform the functions attributed to them herein.

Each of sensors 40 generates a signal as a function of one or more physiological parameters of a patient 12. An IMD 14 may include circuitry (not shown) that conditions the signals generated by sensors 40 such that they may be analyzed by processor 46. For example, an IMD 14 may include one or more analog to digital converters to convert analog signals generated by sensors 40 into digital signals usable by processor 46, as well as suitable filter and amplifier circuitry. Although shown as including two sensors 40, a system 10 may include any number of sensors.

Further, as illustrated in FIGS. 2A and 2B, sensors 40 may be included as part of an IMD 14, or coupled to the IMD 14 via leads 16. Sensors 40 may be coupled to an IMD 14 via therapy leads 16A-16D, or via other leads 16, such as lead 16E depicted in FIGS. 2A and 2B. In some embodiments, a sensor 40 located outside of IMD 14 may be in wireless communication with processor 46. Wireless communication between sensors 40 and IMDs 14 may, as examples, include RF communication or communication via electrical signals conducted through the tissue and/or fluid of a patient 12.

Exemplary physiological parameters of patient 12 that may be monitored by an IMD 14 include activity, posture, heart rate, ECG morphology, respiration rate, respiratory volume, blood pressure, blood oxygen saturation, partial pressure of oxygen within blood, partial pressure of oxygen within cerebrospinal fluid (CSF), muscular activity and tone, core temperature, subcutaneous temperature, arterial blood flow, the level of melatonin within one or more bodily fluids, brain electrical activity, and eye motion. Further, as discussed above, in some external medical device embodiments of the invention, galvanic skin response may additionally or alternatively be monitored. Sensors 40 may be of any type known in the art capable of generating a signal as a function of one or more of these parameters.

Processor 46 may identify when a patient 12 is attempting to sleep in a variety of ways. For example, processor 46 may identify the time that patient begins attempting to fall asleep based on an indication received from a patient 12, e.g., via patient programmer 26 and a telemetry circuit 50. In other embodiments, processor 46 identifies the time that a patient 12 begins attempting to fall asleep based on the activity level of the patient 12.

In such embodiments, an IMD 14 may include one or more sensors 40 that generate a signal as a function of patient activity. For example, sensors 40 may include one or more accelerometers, gyros, mercury switches, or bonded piezoelectric crystals that generates a signal as a function of patient activity, e.g., body motion, footfalls or other impact events, and the like. Additionally or alternatively, sensors 40 may include one or more electrodes that generate an electromyogram (EMG) signal as a function of muscle electrical activity, which may indicate the activity level of a patient. The electrodes may be, for example, located in the legs, abdomen, chest, back or buttocks of a patient 12 to detect muscle activity associated with walking, running, or the like. The electrodes may be coupled to an IMD 14 wirelessly or by leads 16 or, if IMD 14 is implanted in these locations, integrated with a housing of an IMD 14.

However, bonded piezoelectric crystals located in these areas generate signals as a function of muscle contraction in addition to body motion, footfalls or other impact events. Consequently, use of bonded piezoelectric crystals to detect activity of a patient 12 may be preferred in some embodiments in which it is desired to detect muscle activity in addition to body motion, footfalls, or other impact events. Bonded piezoelectric crystals may be coupled to an IMD 14 wirelessly or via leads 16, or piezoelectric crystals may be bonded to the can of the IMD 14 when the IMD is implanted in these areas, e.g., in the back, chest, buttocks or abdomen of a patient 12.

Processor 46 may identify a time when the activity level of a patient 12 falls below a threshold activity level value stored in memory 48, and may determine whether the activity level remains substantially below the threshold activity level value for a threshold amount of time stored in memory 48. In other words, a patient 12 remaining inactive for a sufficient period of time may indicate that patient 12 is attempting to fall asleep. If processor 46 determines that the threshold amount of time is exceeded, processor 46 may identify the time at which the activity level fell below the threshold activity level value as the time that a patient 12 began attempting to fall asleep.

In some embodiments, processor 46 determines whether a patient 12 is attempting to fall asleep based on whether the patient 12 is or is not recumbent, e.g., lying down. In such embodiments, sensors 40 may include a plurality of accelerometers, gyros, or magnetometers oriented orthogonally that generate signals which indicate the posture of a patient 12. In addition to being oriented orthogonally with respect to each other, each of sensors 40 used to detect the posture of a patient 12 may be generally aligned with an axis of the body of the patient 12. In exemplary embodiments, an IMD 14 includes three orthogonally oriented posture sensors 40.

When sensors 40 include accelerometers, for example, that are aligned in this manner, processor 46 may monitor the magnitude and polarity of DC components of the signals generated by the accelerometers to determine the orientation of a patient 12 relative to the Earth's gravity, e.g., the posture of the patient 12. In particular, the processor 46 may compare the DC components of the signals to respective threshold values stored in memory 48 to determine whether a patient 12 is or is not recumbent. Further information regarding use of orthogonally aligned accelerometers to determine patient posture may be found in a commonly assigned U.S. Pat. No. 5,593,431, which issued to Todd J. Sheldon.

Other sensors 40 that may generate a signal that indicates the posture of a patient 12 include electrodes that generate an electromyogram (EMG) signal, or bonded piezoelectric crystals that generate a signal as a function of contraction of muscles. Such sensors 40 may be implanted in the legs, buttocks, abdomen, or back of a patient 12, as described above. The signals generated by such sensors when implanted in these locations may vary based on the posture of a patient 12, e.g., may vary based on whether the patient is standing, sitting, or laying down.

Further, the posture of a patient 12 may affect the thoracic impedance of the patient. Consequently, sensors 40 may include an electrode pair, including one electrode integrated with the housing of an IMD 14 and one of electrodes 42, that generates a signal as a function of the thoracic impedance of the patient 12, and processor 46 may detect the posture or posture changes of the patient 12 based on the signal. The electrodes of the pair may be located on opposite sides of the patient's thorax. For example, the electrode pair may include one of electrodes 42 located proximate to the spine of a patient for delivery of SCS therapy, and an IMD 14 with an electrode integrated in its housing may be implanted in the abdomen of a patient 12.

Additionally, changes of the posture of a patient 12 may cause pressure changes with the cerebrospinal fluid (CSF) of the patient. Consequently, sensors 40 may include pressure sensors coupled to one or more intrathecal or intracerebroventricular catheters, or pressure sensors coupled to an IMD 14 wirelessly or via lead 16. CSF pressure changes associated with posture changes may be particularly evident within the brain of the patient, e.g., may be particularly apparent in an intracranial pressure (ICP) waveform.

In some embodiments, processor 46 considers both the posture and the activity level of patient 12 when determining whether a patient 12 is attempting to fall asleep. For example, processor 46 may determine whether a patient 12 is attempting to fall asleep based on a sufficiently long period of sub-threshold activity, as described above, and may identify the time that patient began attempting to fall asleep as the time when a patient 12 became recumbent. Any of a variety of combinations or variations of these techniques may be used to determine when a patient 12 is attempting to fall asleep, and a specific one or more techniques may be selected based on the sleeping and activity habits of a particular patient.

In other embodiments, processor 46 determines when a patient 12 is attempting to fall asleep based on the level of melatonin in a bodily fluid. In such embodiments, a sensor 40 may take the form of a chemical sensor that is sensitive to the level of melatonin or a metabolite of melatonin in the bodily fluid, and estimate the time that a patient 12 will attempt to fall asleep based on the detection. For example, processor 46 may compare the melatonin level or rate of change in the melatonin level to a threshold level stored in memory 48, and identify the time that threshold value is exceeded. Processor 46 may identify the time that a patient 12 is attempting to fall asleep as the time that the threshold is exceeded, or some amount of time after the threshold is exceeded. Any of a variety of combinations or variations of the above-described techniques may be used to determine when patient 12 is attempting to fall asleep, and a specific one or more techniques may be selected based on the sleeping and activity habits of a particular patient.

When an IMD 14 determines that a patient 12 is attempting to sleep, the IMD 14 may determine values for one or more metrics that indicate the quality of a patient's sleep based on at least one of the above-identified physiological parameters of the patient. In particular, in order to determine values for some sleep quality metrics, an IMD 14 determines when a patient 12 is asleep, e.g., identify the times that the patient 12 falls asleep and wakes up, in addition to when the patient 12 is attempting to fall asleep. The detected values of physiological parameters of a patient 12, such as activity level, heart rate, ECG morphological features, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, brain electrical activity, eye motion, and galvanic skin response may discernibly change when a patient 12 falls asleep or awakes. Some of these physiological parameters may be at low values when a patient 12 is asleep. Further, the variability of at least some of these parameters, such as heart rate and respiration rate, may be at a low value when the patient is asleep.

Consequently, in order to detect when a patient 12 falls asleep and wakes up, processor 46 may monitor one or more of these physiological parameters, or the variability of these physiological parameters, and detect the discernable changes in their values associated with a transition between a sleeping state and an awake state. In some embodiments, processor 46 may determine a mean or median value for a parameter based on values of a signal over time, and determine whether a patient 12 is asleep or awake based on the mean or median value. Processor 46 may compare one or more parameter or parameter variability values to thresholds stored in memory 48 to detect when a patient 12 falls asleep or awakes. The thresholds may be absolute values of a physiological parameter, or time rate of change values for the physiological parameter, e.g., to detect sudden changes in the value of a parameter or parameter variability. In some embodiments, a threshold used by processor 46 to determine whether a patient 12 is asleep may include a time component. For example, a threshold may require that a physiological parameter be above or below a threshold value for a period of time before processor 46 determines that patient is awake or asleep.

In some embodiments, in order to determine whether a patient 12 is asleep, processor 46 monitors a plurality of physiological parameters, and determines a value of a metric that indicates the probability that the patient 12 is asleep for each of the parameters based on a value of the parameter. In particular, the processor 46 may apply a function or look-up table to the current, mean or median value, and/or the variability of each of a plurality of physiological parameters to determine a sleep probability metric for each of the plurality of physiological parameters. A sleep probability metric value may be a numeric value, and in some embodiments may be a probability value, e.g., a number within the range from 0 to 1, or a percentage value.

Processor 46 may average or otherwise combine the plurality of sleep probability metric values to provide an overall sleep probability metric value. In some embodiments, processor 46 may apply a weighting factor to one or more of the sleep probability metric values prior to combination. Processor 46 may compare the overall sleep probability metric value to one or more threshold values stored in memory 48 to determine when a patient 12 falls asleep or awakes. Use of sleep probability metric values to determine when a patient is asleep based on a plurality of monitored physiological parameters is described in greater detail in a commonly-assigned and copending U.S. patent application Ser. No. 11/691,405 by Ken Heruth and Keith Miesel, entitled "DETECTING SLEEP," and filed on Mar. 26, 2007, which is incorporated herein by reference in its entirety.

To enable processor 46 to determine when a patient 12 is asleep or awake, sensors 40 may include, for example, activity sensors as described above. In some embodiments, the activity sensors may include electrodes or bonded piezoelectric crystals, which may be implanted in the back, chest, buttocks, or abdomen of a patient 12 as described above. In such embodiments, processor 46 may detect the electrical activation and contractions of muscles associated with gross motor activity of the patient, e.g., walking, running or the like via the signals generated by such sensors. Processor 46 may also detect spasmodic or pain related muscle activation via the signals generated by such sensors. Spasmodic or pain related muscle activation may indicate that a patient 12 is not sleeping, e.g., unable to sleep, or if the patient 12 is sleeping, may indicate a lower level of sleep quality.

As another example, sensors 40 may include electrodes located on leads or integrated as part of the housing of an IMD 14 that generate an electrogram signal as a function of electrical activity of the heart of a patient 12, and processor 46 may monitor the heart rate of the patient 12 based on the electrogram signal. In other embodiments, a sensor may include an acoustic sensor within an IMD 14, a pressure or flow sensor within the bloodstream or cerebrospinal fluid of a patient 12, or a temperature sensor located within the bloodstream of the patient 12. The signals generated by such sensors may vary as a function of contraction of the heart of a patient 12, and can be used by an IMD 14 to monitor the heart rate of the patient 12.

In some embodiments, processor 46 may detect, and measure values for one or more ECG morphological features within an electrogram generated by electrodes as described above. ECG morphological features may vary in a manner that indicates whether a patient 12 is asleep or awake. For example, the amplitude of the ST segment of the ECG may decrease when patient 12 is asleep. Further, the amplitude of QRS complex or T-wave may decrease, and the widths of the QRS complex and T-wave may increase when a patient 12 is asleep. The QT interval and the latency of an evoked response may increase when a patient 12 is asleep, and the amplitude of the evoked response may decrease when the patient 12 is asleep.

In some embodiments, sensors 40 may include an electrode pair, including one electrode integrated with the housing of an IMD 14 and one of electrodes 42, that generates a signal as a function of the thoracic impedance of a patient 12, as described above, which varies as a function of respiration by the patient 12. In other embodiments, sensors 40 may include a strain gauge, bonded piezoelectric element, or pressure sensor within the blood or cerebrospinal fluid that generates a signal that varies based on patient respiration. An electrogram generated by electrodes as discussed above may also be modulated by patient respiration, and may be used as an indirect representation of respiration rate.

Sensors 40 may include electrodes that generate an electromyogram (EMG) signal as a function of muscle electrical activity, as described above, or may include any of a variety of known temperature sensors to generate a signal as a function of a core or subcutaneous temperature of a patient 12. Such electrodes and temperature sensors may be incorporated within the housing of an IMD 14, or coupled to the IMD 14 wirelessly or via leads. Sensors 40 may also include a pressure sensor within, or in contact with, a blood vessel. The pressure sensor may generate a signal as a function of the a blood pressure of a patient 12, and may, for example, comprise a Chronicle Hemodynamic Monitor™ commercially available from Medtronic, Inc. of Minneapolis, Minn. Further, certain muscles of a patient 12, such as the muscles of the patient's neck, may discernibly relax when the patient 12 is asleep or within certain sleep states. Consequently, sensors 40 may include strain gauges or EMG electrodes implanted in such locations that generate a signal as a function of muscle tone.

Sensors 40 may also include optical pulse oximetry sensors or Clark dissolved oxygen sensors located within, as part of a housing of, or outside of an IMD 14, which generate signals as a function of blood oxygen saturation and blood oxygen partial pressure respectively. In some embodiments, a system 10 may include a catheter with a distal portion located within the cerebrospinal fluid of a patient 12, and the distal end may include a Clark dissolved oxygen sensor to generate a signal as a function of the partial pressure of oxygen within the cerebrospinal fluid (CSF). Embodiments in which an IMD comprises an implantable pump, for example, may include a catheter with a distal portion located in the cerebrospinal fluid.

In some embodiments, sensors 40 may include one or more intraluminal, extraluminal, or external flow sensors positioned to generate a signal as a function of arterial blood flow. A flow sensor may be, for example, an electromagnetic, thermal convection, ultrasonic-Doppler, or laser-Doppler flow sensor. Further, in some external medical device embodiments of the invention, sensors 40 may include one or more electrodes positioned on the skin of a patient 12 to generate a signal as a function of galvanic skin response.

Additionally, in some embodiments, sensors 40 may include one or more electrodes positioned within or proximate to the brain of patient, which detect electrical activity of the brain. For example, in embodiments in which an IMD 14 delivers stimulation or other therapy to the brain, processor 46 may be coupled to electrodes implanted on or within the brain via a lead 16. System 10B, illustrated in FIGS. 1B and 2B, is an example of a system that includes electrodes 42, located on or within the brain of patient 12B, that are coupled to IMD 14B.

As shown in FIG. 2B, electrodes 42 may be selectively coupled to therapy module 44 or an EEG signal module 54 by a multiplexer 52, which operates under the control of processor 46. EEG signal module 54 receives signals from a selected set of the electrodes 42 via multiplexer 52 as controlled by processor 46. EEG signal module 54 may analyze the EEG signal for certain features indicative of sleep or different sleep states, and provide indications of relating to sleep or sleep states to processor 46. Thus, electrodes 42 and EEG signal module 54 may be considered another sensor 40 in system 10B. IMD 14B may include circuitry (not shown) that conditions the EEG signal such that it may be analyzed by processor 52. For example, IMD 14B may include one or more analog to digital converters to convert analog signals received from electrodes 42 into digital signals usable by processor 46, as well as suitable filter and amplifier circuitry.

In some embodiments, processor 46 will only request EEG signal module 54 to operate when one or more other physiological parameters indicate that patient 12B is already asleep. However, processor 46 may also direct EEG signal module to analyze the EEG signal to determine whether patient 12B is sleeping, and such analysis may be considered alone or in combination with other physiological parameters to determine whether patient 12B is asleep. EEG signal module 60 may process the EEG signals to detect when patient 12 is asleep using any of a variety of techniques, such as techniques that identify whether a patient is asleep based on the amplitude and/or frequency of the EEG signals. In some embodiments, the functionality of EEG signal module 54 may be provided by processor 46, which, as described above, may include one or more microprocessors, ASICs, or the like.

In other embodiments, processor 46 may be wirelessly coupled to electrodes that detect brain electrical activity. For example, one or more modules may be implanted beneath the scalp of the patient, each module including a housing, one or more electrodes, and circuitry to wirelessly transmit the signals detected by the one or more electrodes to an IMD 14. In other embodiments, the electrodes may be applied to the patient's scalp, and electrically coupled to a module that includes circuitry for wirelessly transmitting the signals detected by the electrodes to an IMD 14. The electrodes may be glued to the patient's scalp, or a head band, hair net, cap, or the like may incorporate the electrodes and the module, and may be worn by a patient 12 to apply the electrodes to the patient's scalp when, for example, the patient is attempting to sleep. The signals detected by the electrodes and transmitted to an IMD 14 may be electroencephalogram (EEG) signals, and processor 46 may process the EEG signals to detect when a patient 12 is asleep using any of a variety of known techniques, such as techniques that identify whether a patient is asleep based on the amplitude and/or frequency of the EEG signals.

Also, the motion of the eyes of a patient 12 may vary depending on whether the patient is sleeping and which sleep state the patient is in. Consequently, sensors 40 may include electrodes place proximate to the eyes of a patient 12 to detect electrical activity associated with motion of the eyes, e.g., to generate an electro-oculography (EOG) signal. Such electrodes may be coupled to an IMD 14 via one or more leads 16, or may be included within modules that include circuitry to wirelessly transmit detected signals to the IMD 14. Wirelessly coupled modules incorporating electrodes to detect eye motion may be worn externally by a patient 12, e.g., attached to the skin of the patient 12 proximate to the eyes by an adhesive when the patient is attempting to sleep.

Processor 46 may also detect arousals and/or apneas that occur when a patient 12 is asleep based on one or more of the above-identified physiological parameters. For example, processor 46 may detect an arousal based on an increase or sudden increase in one or more of heart rate, heart rate variability, respiration rate, respiration rate variability, blood pressure, or muscular activity as the occurrence of an arousal. Processor 46 may detect an apnea based on a disturbance in the respiration rate of a patient 12, e.g., a period with no respiration.

Processor 46 may also detect arousals or apneas based on sudden changes in one or more of the ECG morphological features identified above. For example, a sudden elevation of the ST segment within the ECG may indicate an arousal or an apnea. Further, sudden changes in the amplitude or frequency of an EEG signal, EOG signal, or muscle tone signal may indicate an apnea or arousal. Memory 48 may store thresholds used by processor 46 to detect arousals and apneas. Processor 46 may determine, as a sleep quality metric value, the number of apnea events and/or arousals during a night.

Further, in some embodiments, processor 46 may determine which sleep state a patient 12 is in during sleep, e.g., REM, S1, S2, S3, or S4, based on one or more of the monitored physiological parameters. In some embodiments, memory 48 may store one or more thresholds for each of sleep states, and processor 46 may compare physiological parameter or sleep probability metric values to the thresholds to determine which sleep state a patient 12 is currently in. Further, in some embodiments, processor 46 may use any of a variety of known techniques for determining which sleep state patient is in based on an EEG signal, which processor 46 may receive via electrodes as described above, such as techniques that identify sleep state based on the amplitude and/or frequency of the EEG signals. In some embodiments, processor 46 may also determine which sleep state patient is in based on an EOG signal, which processor 46 may receive via electrodes as described above, either alone or in combination with an EEG signal, using any of a variety of techniques known in the art. Processor 46 may determine, as sleep quality metric values, the amounts of time per night spent in the various sleep states.

The S3 and S4 sleep states may be of particular importance to the quality of sleep experienced by a patient 12. Interruption from reaching these states, or inadequate time per night spent in these states, may cause a patient 12 to not feel rested. For this reason, the S3 and S4 sleep states are believed to provide the "refreshing" part of sleep.

In some cases, interruption from reaching the S3 and S4 sleep states, or inadequate time per night spent in these states has been demonstrated to cause normal subjects to exhibit some symptoms of fibromyalgia. Also, subjects with fibromyalgia usually do not reach these sleep states. For these reasons, in some embodiments, an IMD 14 may determine an amount or percentage of time spent in one or both of the S3 and S4 sleep states as a sleep quality metric.

When processor 46 determines that a patient 12 is not attempting to sleep, processor 46 periodically determines activity levels of the patient. For example, a sensor 40 may be an accelerometer, a bonded piezoelectric crystal, a mercury switch, or a gyro, and processor 46 may determine an activity level based on a signal generated by one of these types of sensors 40 by sampling the signal and determining a number of activity counts during the sample period. Processor 46 may then store the determined number of activity counts in memory 48 as an activity level.

For example, processor 46 may compare the sample of a signal generated by an accelerometer or piezoelectric crystal to one or more amplitude thresholds stored within memory 48. Processor 46 may identify each threshold crossing as an activity count. Where processor 46 compares the sample to multiple thresholds with varying amplitudes, processor 46 may identify crossing of higher amplitude thresholds as multiple activity counts. Using multiple thresholds to identify activity counts, processor 46 may be able to more accurately determine the extent of patient activity for both high impact, low frequency and low impact, high frequency activities. In embodiments in which a sensor 40 takes the form of a mercury switch, processor 46 may identify the number of switch contacts indicated during the sample period as the number of activity counts.

In embodiments in which a sensor 40 comprises an accelerometer or piezoelectric crystal, an IMD 14 may include a filter (not shown), or processor 46 may apply a digital filter, that passes a band from approximately 0.1 Hz to 10 Hz. The filter may reduce noise in the signal, and pass the portion of the signal that reflects patient activity.

In some embodiments, the processor 46 may monitor a signal that indicates a physiological parameter of a patient 12, which in turn varies as a function of patient activity. For example, in some embodiments, sensors 40 may includes one or more sensors that generate a signal that indicates the heart rate, ECG morphology, respiration rate, respiratory volume, or muscular activity of the patient, as described above. In such embodiments, processor 46 may periodically determine the heart rate, values of ECG morphological features, respiration rate, respiratory volume, or muscular activity level of a patient 12 based on the signal. The determined values of these parameters may be mean or median values.

In some embodiments, processor 46 compares a determined value of such a physiological parameter to one or more thresholds or a look-up table stored in memory to determine a number of activity counts, and stores the determined number of activity counts in memory 48 as a determined activity level. In other embodiments, processor 46 may store the determined physiological parameter value as a determined activity level. The use of activity counts, however, may allow processor 46 to determine an activity level based on a plurality of signals generated by a plurality of sensors 40. For example, processor 46 may determine a first number of activity counts based on a sample of an accelerometer signal and a second number of activity counts based on a heart rate determined from an electrogram signal at the time the accelerometer signal was sampled. Processor 46 may determine an activity level by calculating the sum or average, which may be a weighted sum or average, of first and second activity counts.

Processor 46 may record activity levels continuously or periodically, e.g., one sample every minute or continuously for ten minutes each hour. Further processor 46 need not determine sleep quality metrics each time a patient 12 attempts to sleep, or record activity levels each time the patient 12 is not attempting to sleep. In some embodiments, processor 46 may record activity levels and determine sleep quality metric values in response to receiving an indication from a patient 12 via patient programmer 26. A patient 12 may provide the indication by depressing a button or otherwise manipulating user input media on programmer 26. For example, processor 46 may record activity levels and sleep quality metrics during times when a patient 12 believes the therapy delivered by an IMD 14 is ineffective and/or the symptoms experienced by the patient 12 have worsened. In this manner, processor 46 may limit data collection to periods in which more probative data is likely to be collected, and thereby conserve a battery and/or storage space within memory 48.

In some embodiments, processor 46 determines a value of one or more activity metrics based on determined activity levels and stores the activity metric values within memory 48. For example, processor 46 may determine a mean or median of activity levels, and store the mean or median activity level as an activity metric value. In embodiments in which activity levels comprise activity counts, processor 46 may store, for example, an average number of activity counts per unit time as an activity metric value.

In other embodiments, processor 46 may compare a mean or median activity level to one or more threshold values, and may select an activity metric value from a predetermined scale of activity metric values based on the comparison. The scale may be numeric, such as activity metric values from 1-10, or qualitative, such as low, medium or high activity. The scale of activity metric values may be, for example, stored as a look-up table within memory 48. Processor 46 stores the activity metric value selected from the scale within memory 48.

In some embodiments, processor 46 compares a number of activity levels to one or more threshold values. Based on the comparison, processor 46 may determine percentages of time above and/or below the thresholds, or within threshold ranges. Processor 46 may store the determined percentages within memory 48 as one or more activity metric values. In other embodiments, processor 46 compares a number of activity levels to a threshold value, and determines an average length of time that consecutively recorded activity levels remained above the threshold as an activity metric value.

Figure 3:
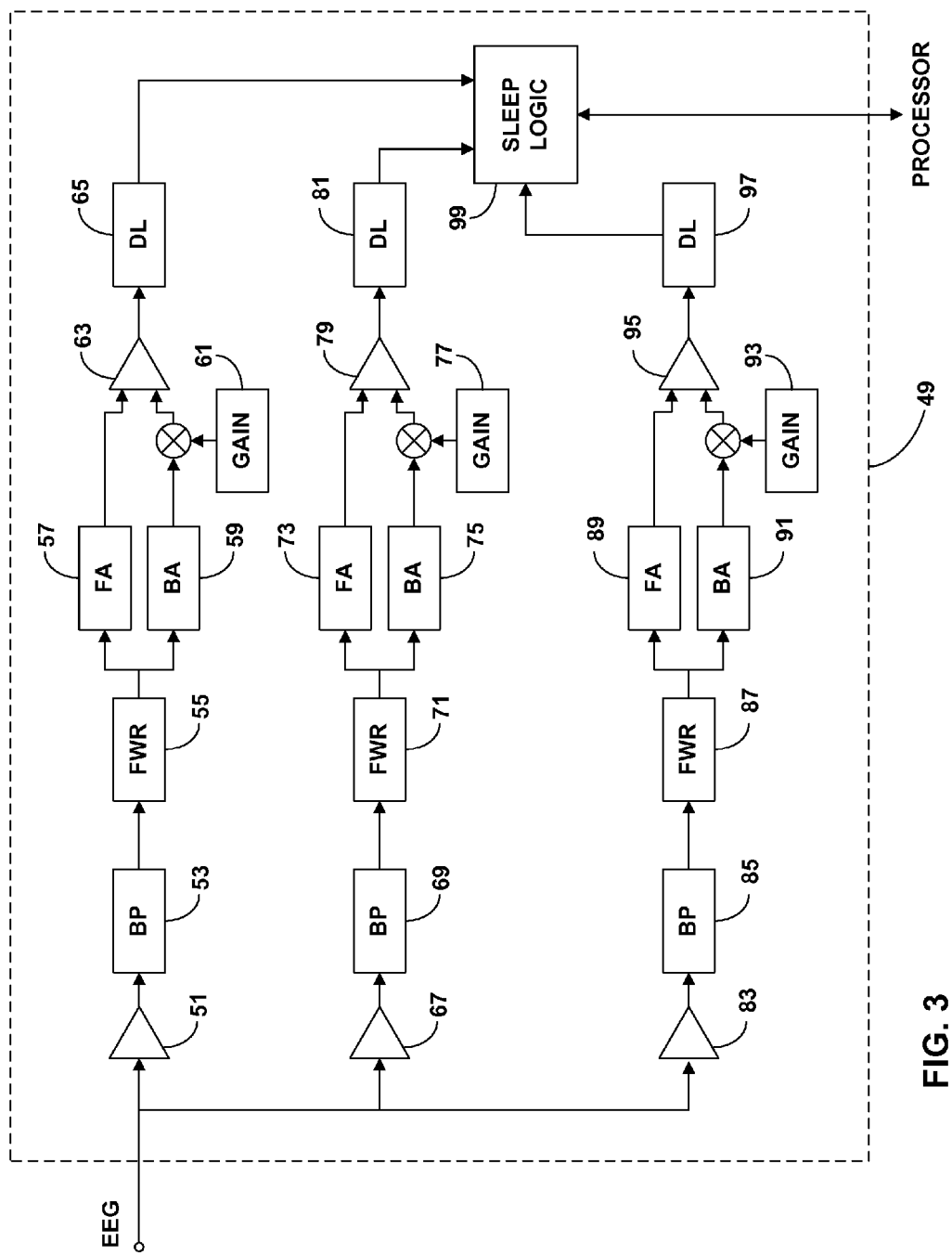
FIG. 3 is a logic diagram illustrating an example circuit that detects the sleep state of a patient from the electroencephalogram (EEG) signal.

FIG. 3 is a logical diagram of an example circuit that detects sleep and/or the sleep type of a patient based on the electroencephalogram (EEG) signal. As shown in FIG. 3, module 49 may be integrated into an EEG signal module of an IMD 14 or a separate implantable or external device capable of detecting an EEG signal. An EEG signal detected by electrodes adjacent to the brain of a patient 12 is transmitted into module 49 and provided to three channels, each of which includes a respective one of amplifiers 51, 67 and 83, and bandpass filters 53, 69 and 85. In other embodiments, a common amplifier amplifies the EEG signal prior to filters 53, 69 and 85.

Bandpass filter 53 allows frequencies between approximately 4 Hz and approximately 8 Hz, and signals within the frequency range may be prevalent in the EEG during S1 and S2 sleep states. Bandpass filter 69 allows frequencies between approximately 1 Hz and approximately 3 Hz, which may be prevalent in the EEG during the S3 and S4 sleep states. Bandpass filter 85 allows frequencies between approximately 10 Hz and approximately 50 Hz, which may be prevalent in the EEG during REM sleep. Each resulting signal may then be processed to identify the current sleep state of a patient 12.

After bandpass filtering of the original EEG signal, the filtered signals are similarly processed in parallel before being delivered to sleep logic module 99. For ease of discussion, only one of the three channels will be discussed herein, but each of the filtered signals would be processed similarly.

Once the EEG signal is filtered by bandpass filter 53, the signal is rectified by full-wave rectifier 55. Modules 57 and 59 respectively determine the foreground average and background average so that the current energy level can be compared to a background level at comparator 63. The signal from background average is increased by gain 61 before being sent to comparator 63, because comparator 63 operates in the range of millivolts or volts while the EEG signal amplitude is originally on the order of microvolts. The signal from comparator 63 is indicative of sleep stages S1 and S2. If duration logic 65 determines that the signal is greater than a predetermined level for a predetermined amount of time, the signal is sent to sleep logic module 99 indicating that patient 12 may be within the S1 or S2 sleep states. In some embodiments, as least duration logic 65, 81, 97 and sleep logic 99 may be embodied in a processor of the device containing EEG module 49.

Module 49 may detect all sleep types for a patient 12. Further, the beginning of sleep may be detected by module 49 based on the sleep state of a patient 12. Some of the components of module 49 may vary from the example of FIG. 3. For example, gains 61, 77 and 93 may be provided from the same power source. Module 49 may be embodied as analog circuitry, digital circuitry, or a combination thereof.

In other embodiments, FIG. 3 may not need to reference the background average to determine the current state of sleep of a patient 12. Instead, the power of the signals from bandpass filters 53, 69 and 85 are compared to each other, and sleep logic module 99 determines which the sleep state of patient 12 based upon the frequency band that has the highest power. In this case, the signals from full-wave rectifiers 55, 71 and 87 are sent directly to a device that calculates the signal power, such as a spectral power distribution module (SPD), and then to sleep logic module 99 which determines the frequency band of the greatest power, e.g., the sleep state of a patient 12. In some cases, the signal from full-wave rectifiers 55, 71 and 87 may be normalized by a gain component to correctly weight each frequency band.

Figure 4:
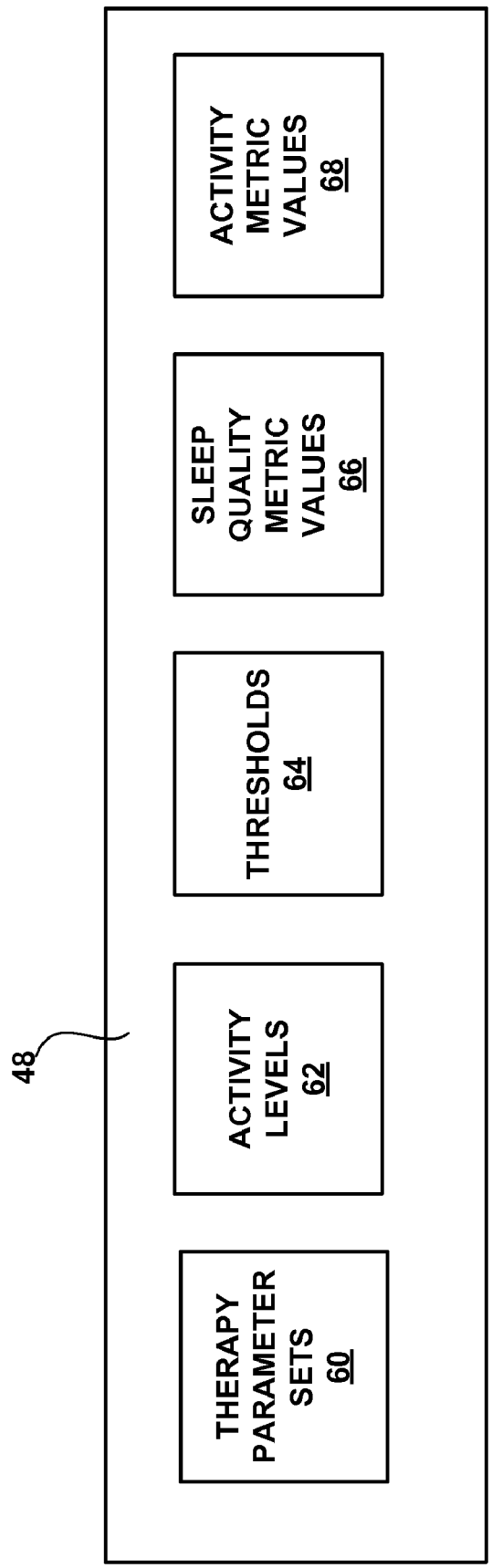
FIG. 4 is a block diagram illustrating an example memory of the implantable medical device of FIG. 1.

FIG. 4 further illustrates memory 48 of an IMD 14. As illustrated in FIG. 4, memory 48 stores information describing a plurality of therapy parameter sets 60. Therapy parameter sets 60 may include parameter sets specified by a clinician using clinician programmer 20. Therapy parameter sets 60 may also include parameter sets that are the result of a patient 12 changing one or more parameters of one of the preprogrammed therapy parameter sets.

Memory 48 also stores the activity levels 62, sleep quality metric values 66, and activity metric values 68 determined by processor 46, as described herein, and threshold values 64 used by processor 46 to determine activity levels 62, sleep quality metric values 66, and activity metric values 68, as described herein. In some embodiments, memory 48 also stores one or more functions or look-up tables (not shown) used by processor 46 to determine sleep probability metric values, activity levels 62, sleep quality metric values 66, and activity metric values 68, as described herein.

Processor 46 may store each sleep quality metric value determined within memory 48 as a sleep quality metric value 66, or may store mean or median sleep quality metric values over periods of time such as days, weeks or months as sleep quality metric values 66. Further, processor 46 may apply a function or look-up table to a plurality of sleep quality metric values to determine overall sleep quality metric value, and may store the overall sleep quality metric values within memory 48. The application of a function or look-up table by processor 46 for this purpose may involve the use or weighting factors for one or more of the individual sleep quality metric values.

Similarly, in some embodiments, processor 46 determines a plurality of activity metric values, and determines an overall activity metric value for a parameter set based on the values of the individual activity metrics for that parameter set. For example, processor 46 may use the plurality of individual activity metric values as indices to identify an overall activity metric value from a look-up table stored in memory 48. Processor 46 may select the overall metric value from a predetermined scale of activity metric values, which may be numeric, such as activity metric values from 1-10, or qualitative, such as low, medium or high activity.

In some embodiments, processor 46 identifies which of therapy parameter sets 60 is currently selected for use in delivering therapy to a patient 12 when an activity level 62 or sleep quality metric value 66 is collected, and may associate that value or level with the current therapy parameter set. For example, for each of the plurality of therapy parameter sets 60, processor 46 may store a representative value of each of one or more sleep quality metrics within memory 48 as a sleep quality metric value 66 with an indication of the therapy parameter set with which that representative value is associated. A representative value of sleep quality metric for a therapy parameter set may be the mean or median of collected sleep quality metric values that have been associated with that therapy parameter set. Further, processor 46 may determine a value of one or more activity metrics for each of therapy parameter sets 60 based on activity levels 62 associated with that therapy parameter set, and may store the associated activity metric values 68 within memory 48.

As shown in FIGS. 2A and 2B, an IMD 14 also includes a telemetry circuit 50 that allows processor 46 to communicate with clinician programmer 20 and patient programmer 26. Processor 46 may receive information identifying therapy parameter sets 60 preprogrammed by the clinician and threshold values 64 from clinician programmer 20 via telemetry circuit 50 for storage in memory 48. Processor 46 may receive an indication of the therapy parameter set 60 selected by a patient 12 for delivery of therapy, or adjustments to one or more of therapy parameter sets 60 made by a patient 12, from patient programmer 26 via telemetry circuit 50. Programmers 20, 26 may receive sleep quality metric values 66 and activity metric values 68 from processor 46 via telemetry circuit 50.

Figure 5:
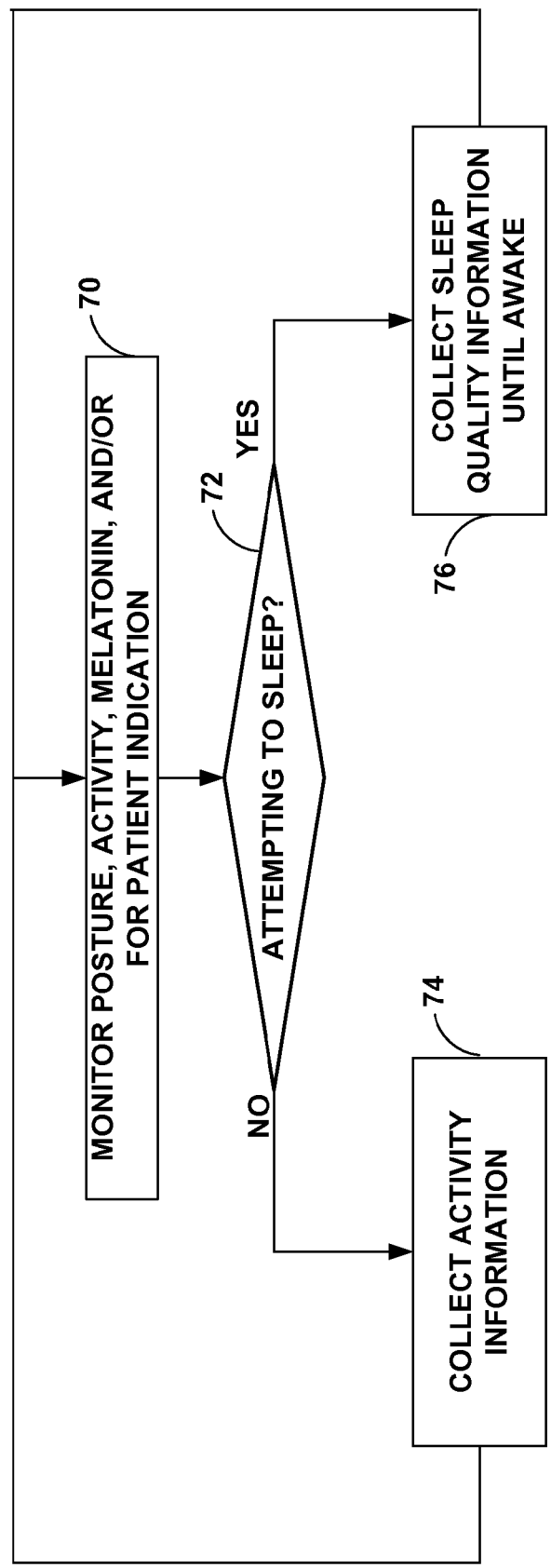
FIG. 5 is a flow diagram illustrating an example method for collecting sleep quality information and activity information that may be employed by an implantable medical device.

FIG. 5 is a flow diagram illustrating an example method for collecting sleep quality information and activity information that may be employed by an IMD 14. An IMD 14 monitors the posture, activity level, and/or melatonin level of a patient 12, or monitors for an indication from the patient 12, e.g., via patient programmer 26 (70), and determines whether the patient 12 is attempting to fall asleep based on the posture, activity level, and/or a patient indication, as described above (72). When an IMD 14 determines that a patient 12 is not attempting to fall asleep, the IMD 14 collects activity information, e.g., periodically determines activity levels 62 (74). When an IMD 14 determines that a patient 12 is attempting to fall asleep, the IMD 14 collects sleep quality information, e.g., determines sleep quality metric values, until the patient 12 is determined to be awake (76).

As discussed above, an IMD 14 need not collect sleep information each time a patient 12 attempts to sleep, or record activity levels each time the patient 12 is not attempting to sleep. In some embodiments, an IMD 14 may record activity levels and determine sleep quality metric values in response to receiving an indication from a patient 12 via patient programmer 26. For example, an IMD 14 may record activity levels and sleep quality metrics during times when a patient 12 believes the therapy delivered by the IMD 14 is ineffective and/or the symptoms experienced by the patient 12 have worsened. In this manner, an IMD 14 may limit data collection to periods in which more probative data is likely to be collected, and thereby conserve a battery and/or storage space within memory 48.

Figure 6:
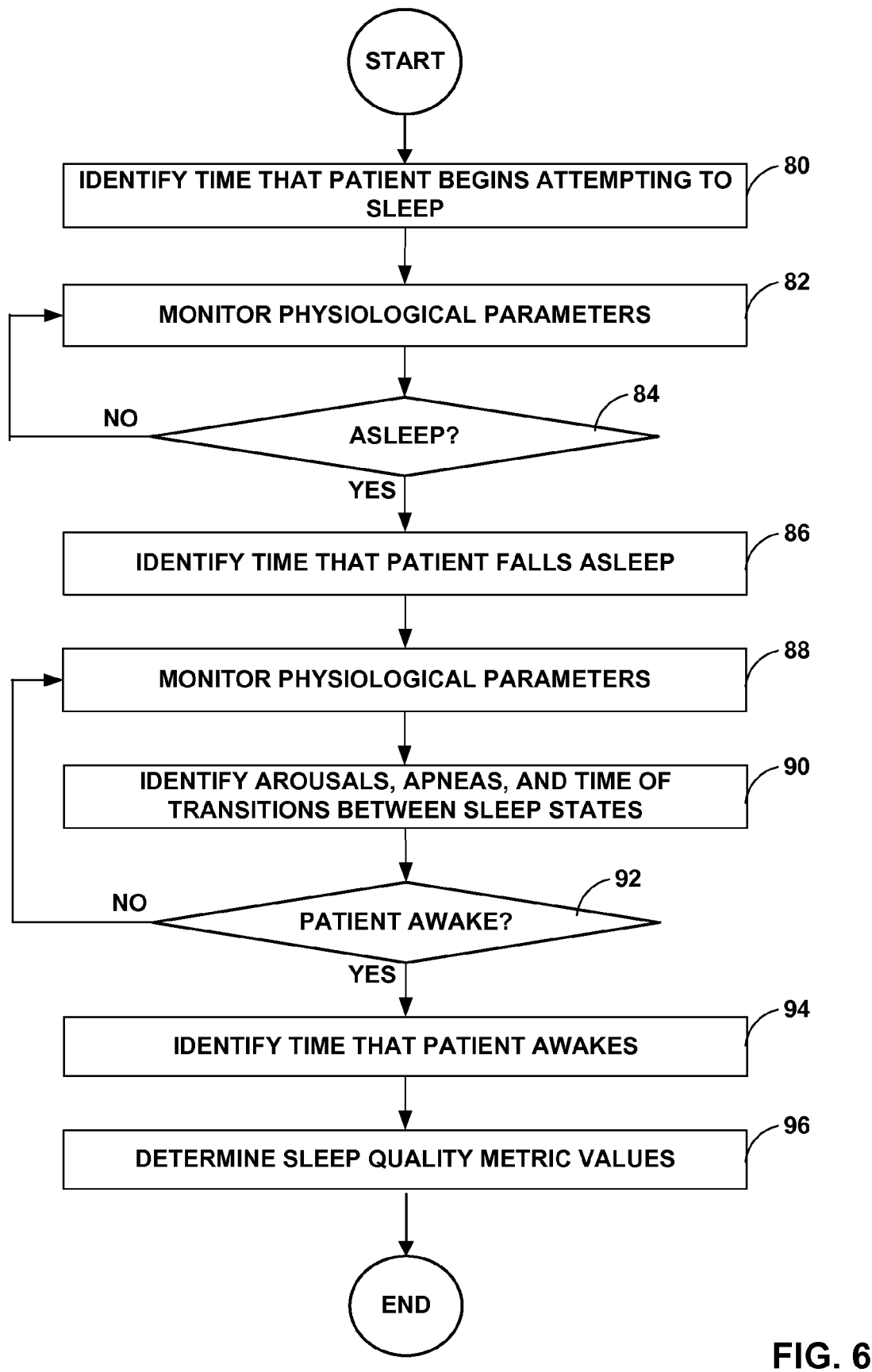
FIG. 6 is a flow diagram illustrating an example method for collecting sleep quality information that may be employed by an implantable medical device.

FIG. 6 is a flow diagram illustrating an example method for collecting sleep quality information that may be employed by an IMD 14. When an IMD 14 determines that a patient 12 is attempting to fall asleep (FIG. 3), the IMD 14 identifies the time that a patient 12 began attempting to fall asleep using any of the techniques described above (80), and monitors one or more of the various physiological parameters of the patient 12 discussed above to determine whether the patient 12 is asleep (82, 84).

In some embodiments, an IMD 14 compares parameter values or parameter variability values to one or more threshold values 64 to determine whether a patient 12 is asleep. In other embodiments, an IMD 14 applies one or more functions or look-up tables to determine one or more sleep probability metric values based on the physiological parameter values, and compares the sleep probability metric values to one or more threshold values 64 to determine whether a patient 12 is asleep. While monitoring physiological parameters (82) to determine whether a patient 12 is asleep (84), an IMD 14 may continue to monitor the posture and/or activity level of the patient 12 to confirm that the patient 12 is still attempting to fall asleep.

When an IMD 14 determines that a patient 12 is asleep, e.g., by analysis of the various parameters contemplated herein, the IMD 14 will identify the time that the patient 12 fell asleep (86). While a patient 12 is sleeping, an IMD 14 will continue to monitor physiological parameters of the patient 12 (88). As discussed above, an IMD 14 may identify the occurrence of arousals and/or apneas based on the monitored physiological parameters (90). Further, an IMD 14 may identify the time that transitions between sleep states, e.g., REM, S1, S2, S3, and S4, occur based on the monitored physiological parameters (90).

Additionally, while a patient 12 is sleeping, an IMD 14 monitors physiological parameters of the patient 12 (88) to determine whether the patient 12 has woken up (92). When an IMD 14 determines that a patient 12 is awake, the IMD 14 identifies the time that the patient 12 awoke (94), and determines sleep quality metric values based on the information collected while the patient 12 was asleep (96).

For example, one sleep quality metric value an IMD 14 may calculate is sleep efficiency, which the IMD 14 may calculate as a percentage of time during which the patient 12 is attempting to sleep that the patient 12 is actually asleep. An IMD 14 may determine a first amount of time between the time the IMD 14 identified that a patient 12 fell asleep and the time the IMD 14 identified that the patient 12 awoke. An IMD may also determine a second amount of time between the time the IMD 14 identified that a patient 12 began attempting to fall asleep and the time the IMD 14 identified that the patient 12 awoke. To calculate the sleep efficiency, an IMD 14 may divide the first time by the second time.

Another sleep quality metric value that an IMD 14 may calculate is sleep latency, which the IMD 14 may calculate as the amount of time between the time the IMD 14 identified that a patient 12 was attempting to fall asleep and the time the IMD 14 identified that the patient 12 fell asleep. Other sleep quality metrics with values determined by an IMD 14 based on the information collected by the IMD 14 in the illustrated example include: total time sleeping per day, at night, and during daytime hours; number of apnea and arousal events per occurrence of sleep; and amount of time spent in the various sleep states, e.g., the S3 and S4 sleep states. An IMD 14 may store the determined values as sleep quality metric values 66 within memory 48.

Figure 7:
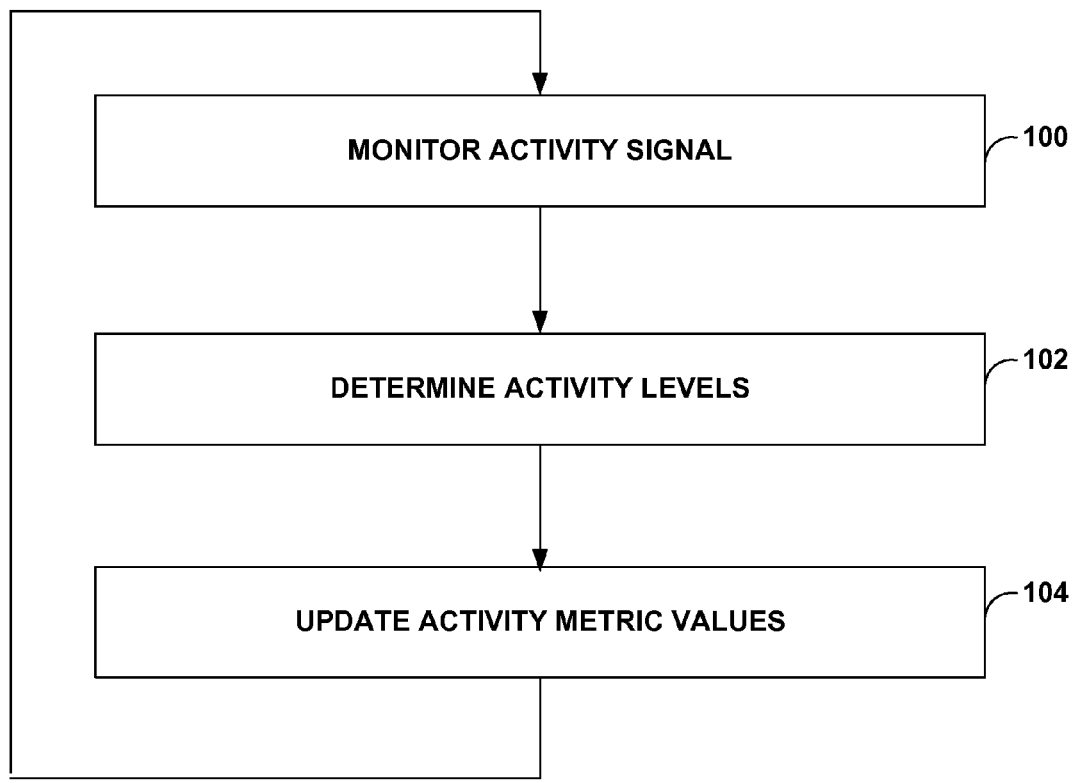
FIG. 7 is a flow diagram illustrating an example method for collecting activity information that may be employed by an implantable medical device.

FIG. 7 is a flow diagram illustrating an example method for collecting activity information that may be employed by an IMD 14. An IMD 14 monitors one or more signals that reflect patient activity generated by sensors 40 (100). For example, an IMD 14 may monitor a signal generated by an accelerometer or piezoelectric crystal, and/or a signal that indicates a physiological parameter that varies as a function of patient activity, such as heart rate, ECG morphology, respiration rate, respiratory volume, or muscle activity.

An IMD 14 determines an activity level 62 (102) based on the one or more signals. For example, an IMD 14 may determine a number of activity counts based on the one or more signals, as described above. An IMD 14 may then update one or more activity metric values 66 based on the determined activity level (104).

An IMD 14 may periodically perform the method illustrated in FIG. 7, i.e., periodically determine activity levels 62. An IMD 14 need not update activity metric values 66 each time an activity level 62 is determined. In some embodiments, for example, an IMD 14 may store activity levels 62 within memory, and may determine the activity metric values 66 upon receiving a request for the values from clinician programmer 20.

Figure 8:
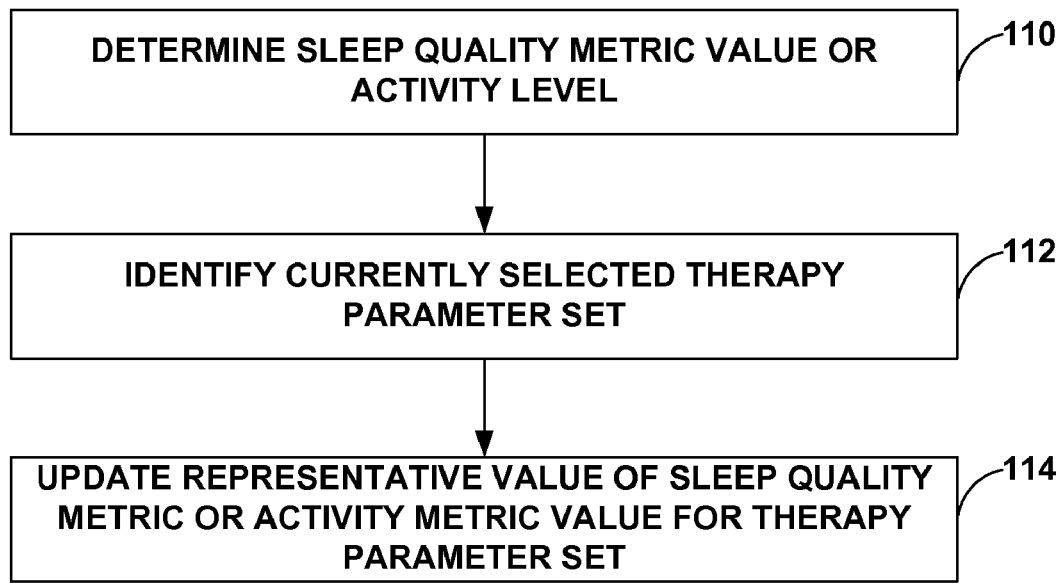
FIG. 8 is a flow diagram illustrating an example method for associating sleep quality information and activity information with therapy parameter sets that may be employed by an implantable medical device.

FIG. 8 is a flow diagram illustrating an example method for associating sleep quality information and activity information with therapy parameter sets that may be employed by an IMD 14. An IMD 14 determines a value 66 of a sleep quality metric or an activity level 62 according to any of the techniques described above (110). An IMD 14 also identifies the current therapy parameter set 60, e.g., the therapy parameter set 60 used by the IMD 14 to control delivery of therapy when a patient 12 was asleep or when the activity level was determined (112), and associates the newly determined level or value with the current therapy parameter set 60.

Among sleep quality metric values 66 within memory 48, an IMD 14 stores a representative value of the sleep quality metric, e.g., a mean or median value, for each of the plurality of therapy parameter sets 60. When an IMD 14 determines a new sleep quality metric value, the IMD 14 updates the representative values for the current therapy parameter set based on the newly determined sleep quality metric value (114). For example, a newly determined sleep efficiency value may be used to determine a new average sleep efficiency value for the current therapy parameter set 60. Similarly, among the activity metric values 68 within memory 48, an IMD 14 stores an associated activity metric value. When an IMD 14 determines a new activity level 62, the IMD 14 updates the activity metric value 68 the current therapy parameter set based on the newly determined activity level.

Figure 9:
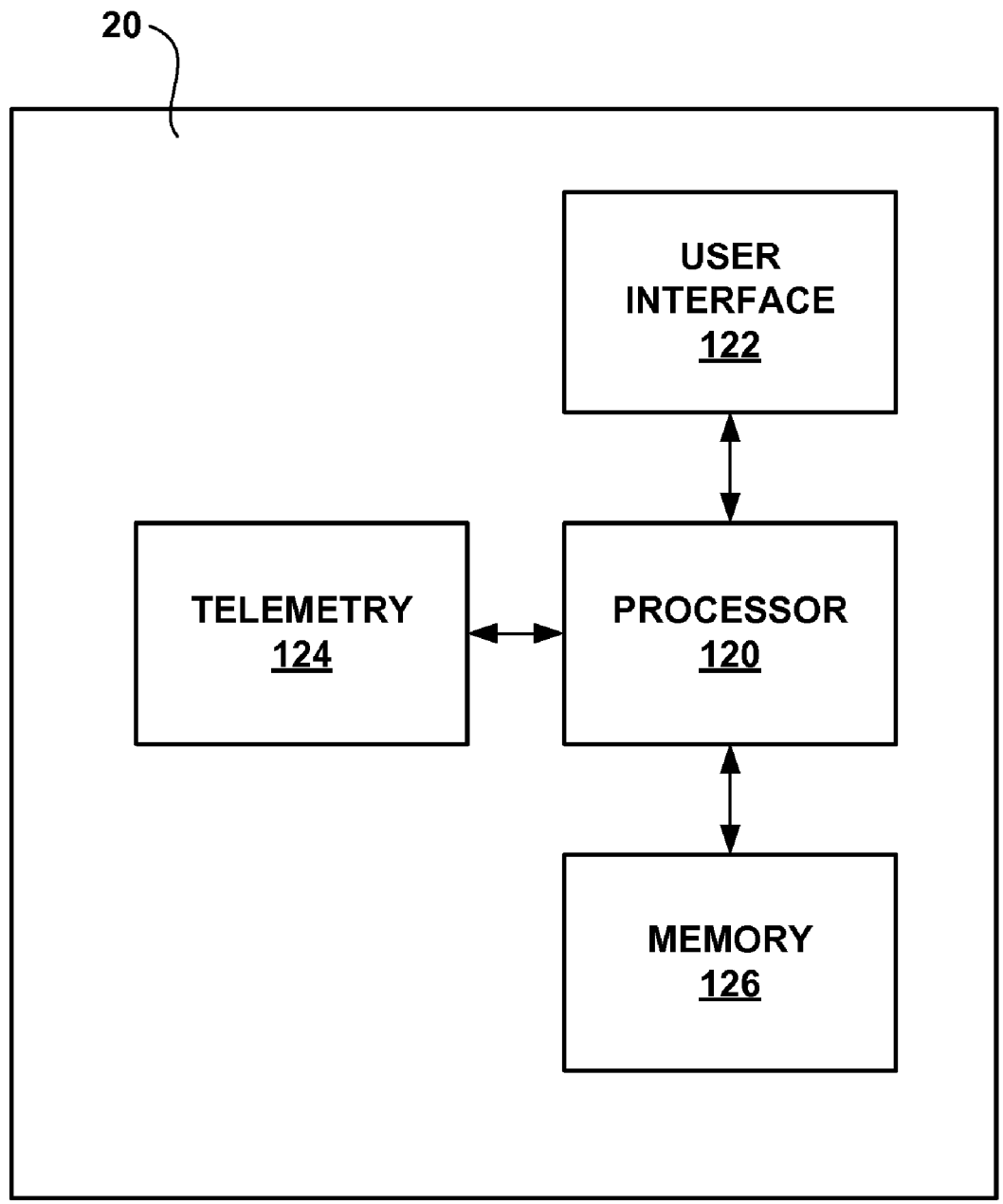
FIG. 9 is a block diagram illustrating an example clinician programmer.

FIG. 9 is a block diagram further illustrating clinician programmer 20. A clinician may interact with a processor 120 via a user interface 122 in order to program therapy for a patient 12, e.g., specify therapy parameter sets. Processor 120 may provide the specified therapy parameter sets to an IMD 14 via telemetry circuit 124.

At another time, e.g., during a follow up visit, processor 120 may receive activity levels 62, sleep quality metric values 66, and/or activity metric values 68 from an IMD 14 via a telemetry circuit 124, and may generate sleep quality information or activity information for presentation to the clinician via user interface 122. For example, processor 120 may present a trend diagram of activity levels 62 or sleep quality metric values 66 over time, or a histogram, pie chart, or other illustration of percentages of time that activity levels 62 or sleep quality metric values 66 were within certain ranges. Processor 120 may generate such charts or diagrams using activity levels 62 and sleep quality metric values 66 associated with a particular one of the therapy parameter sets 60, or all of the activity levels 62 and sleep quality metric values 66 recorded by an IMD 14.

Processor 120 may also receive information identifying a plurality of therapy parameter sets 60, and representative sleep quality metric values 66 and activity metric values associated with the therapy parameter sets 60, from an IMD 14 via telemetry circuit 124. The therapy parameter sets 60 may include the originally specified parameter sets, and parameter sets resulting from manipulation of one or more therapy parameters by a patient 12 using patient programmer 26. After receiving this information, processor 120 generates a list of the therapy parameter sets 60 and associated sleep quality metric values 66 and activity metric values 68, and presents the list to the clinician via user interface 122.

User interface 112 may include display 22 and keypad 24, and may also include a touch screen or peripheral pointing devices as described above. Processor 110 may include a microprocessor, a controller, a DSP, an ASIC, an FPGA, discrete logic circuitry, or the like. Clinician programmer 20 also includes a memory 116. Memory 116 may include program instructions that, when executed by processor 110, cause clinician programmer 20 to perform the functions ascribed to clinician programmer 20 herein. Memory 116 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

FIG. 10 illustrates an example list 130 of therapy parameter sets 60, associated sleep quality metric values 66, and associated activity metric values 68 that may be presented to a clinician by clinician programmer 20. Each row of example list 130 includes an identification of one of therapy parameter sets 60, the parameters of the set, a representative value for one or more sleep quality metrics associated with the identified therapy parameter set, and an associated value of at least one activity metric.

List 130 may include values for any number of sleep quality metrics and activity metrics. The illustrated example list 130 includes sleep efficiency, sleep latency and a percentage of time active. An IMD 14 may determine the percentage of time active for one of parameter sets 60 by, for example, comparing each activity level 62 associated with the parameter set to an "active" threshold, i.e., a threshold indicative of significant physical activity, and determining the percentage of activity levels 62 above the threshold. As illustrated in FIG. 10, an IMD 14 may also compare each activity level for the therapy parameter set to an additional, "high activity" threshold, and determine a percentage of activity levels 62 above that threshold.

Figure 11:
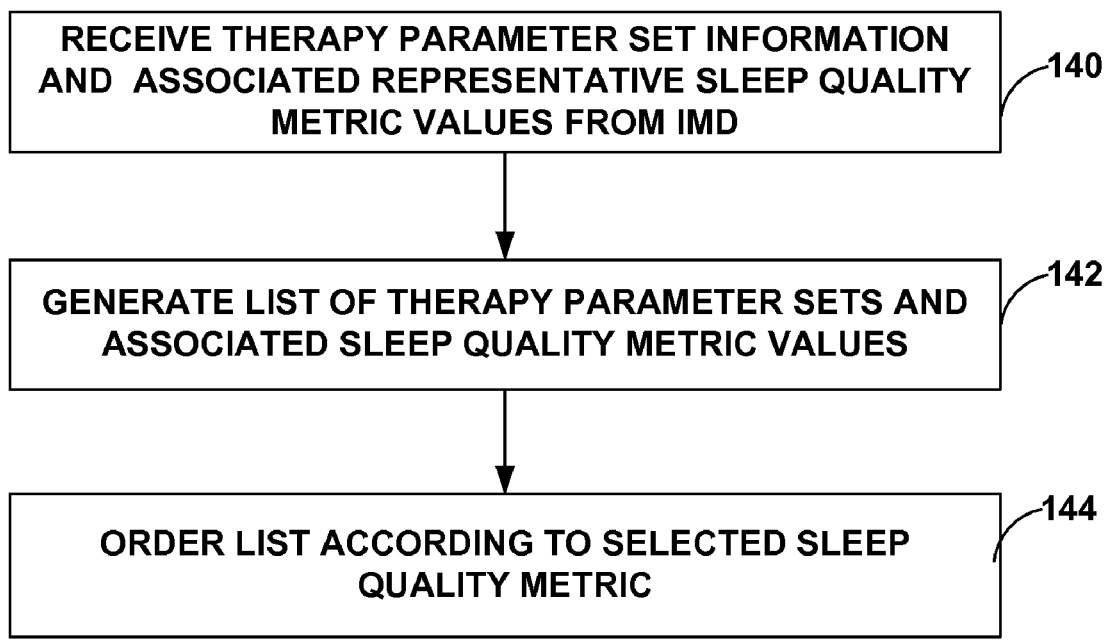
FIG. 11 is a flow diagram illustrating an example method for displaying a list of therapy parameter sets and associated sleep quality information and activity information that may be employed by a clinician programmer.

FIG. 11 is a flow diagram illustrating an example method for displaying a list 130 of therapy parameter sets and associated sleep quality and activity information that may be employed by clinician programmer 20. According to the example method, clinician programmer 20 receives information identifying the plurality of therapy parameter sets 60 stored in memory 48 of an IMD 14, one or more representative sleep quality metric values associated with each of the therapy parameter sets, and one or more activity metric values associated with each of the activity sets (140). Clinician programmer 20 generates a list 130 of the therapy parameter sets 60, any associated representative sleep quality metric values, and any associated activity metric values (142), and orders the list according to a selected one of the sleep quality metrics or activity metrics (144). For example, in the example list 130 illustrated in FIG. 10, the clinician may select whether list 130 should be ordered according to sleep efficiency, sleep latency, or percentage of time active via user interface 122 of clinician programmer 20.

Various embodiments of the invention have been described. However, one skilled in the art will recognize that various modifications may be made to the described embodiments without departing from the scope of the invention. For example, a patient programming device, such as patient programmer 26, may additionally or alternatively receive sleep quality metric values and/or activity metric values from an IMD 14, and may provide sleep quality or activity information to a user based on the sleep quality or activity metric values. Further details regarding provision of sleep quality information to a patient via a patient programming device may be found in a commonly-assigned and copending U.S. patent application Ser. No. 11/691,376 by Ken Heruth and Keith Miesel, entitled "COLLECTING SLEEP QUALITY INFORMATION VIA A MEDICAL DEVICE," filed on Mar. 26, 2007 and published as U.S. patent application publication no. 2007/0276439, which is incorporated herein by reference in its entirety.

As another example, although described herein primarily in the context of treatment with an implantable neurostimulator, the invention is not so limited. The invention may be embodied in any implantable medical device, such as a cardiac pacemaker, an implantable pump, or an implantable monitor that does not itself deliver a therapy to the patient. Further, the invention may be implemented via an external, e.g., non-implantable, medical device.

As discussed above, the ability of a patient to experience quality sleep, e.g., the extent to which the patient able to achieve adequate periods of undisturbed sleep in deeper, more restful sleep states, may be negatively impacted by any of a variety of ailments or symptoms. Further, the overall activity level of a patient, e.g., the extent to which the patient is on his or her feet and moving or otherwise active, rather than sitting or lying in place, may be negatively impacted by any of a variety of ailments or symptoms. Accordingly, the sleep quality and overall activity level of a patient may reflect the progression, status, or severity of the ailment or symptom. Further, the sleep quality of the patient or extent that a patient is active may reflect the efficacy of a particular therapy or therapy parameter set in treating the ailment or symptom. In other words, it may generally be the case that the more efficacious a therapy or therapy parameter set is, the higher quality of sleep the patient will experience, and the more active a patient will be.

As discussed above, in accordance with the invention, sleep quality and activity metrics may be monitored, and used to evaluate the status, progression or severity of an ailment or symptom, or the efficacy of therapies or therapy parameter sets used to treat the ailment or symptom. As an example, chronic pain may cause a patient to have difficulty falling asleep, experience arousals during sleep, or have difficulty experiencing deeper sleep states. Additionally, chronic pain may cause a patient to avoid particular activities, high levels of activity, or activity in general. Systems according to the invention may monitor sleep quality and activity metrics to evaluate the extent to which the patient is experiencing pain.

In some embodiments, systems according to the invention may include any of a variety of medical devices that deliver any of a variety of therapies to treat chronic pain, such as SCS, DBS, cranial nerve stimulation, peripheral nerve stimulation, or one or more drugs. Systems may use the techniques of the invention described above to determine sleep quality and activity metrics for the patient and evaluate such therapies, e.g., by associating values for the metric with therapy parameter sets for delivery of such therapies. Systems according to the invention may thereby evaluate the extent to which a therapy or therapy parameter set is alleviating chronic pain by evaluating the extent to which the therapy or therapy parameter set improves sleep quality for the patient, and allows the patient to be more active or engage in particular activities.

As another example, psychological disorders may cause a patient to experience low sleep quality and, particularly in the case of depression, be less active. Accordingly, embodiments of the invention may determine sleep quality and activity metrics to track the status or progression of a psychological disorder, such as depression, mania, bipolar disorder, or obsessive-compulsive disorder. Further, systems according to the invention may include any of a variety of medical devices that deliver any of a variety of therapies to treat a psychological disorder, such as DBS, cranial nerve stimulation, peripheral nerve stimulation, vagal nerve stimulation, or one or more drugs. Systems may use the techniques of the invention described above to associate sleep quality and activity metric values with the therapies or therapy parameter sets for delivery of such therapies, and thereby evaluate the extent to which a therapy or therapy parameter set is alleviating the psychological disorder by evaluating the extent to which the therapy parameter set improves the sleep quality of the patient, and the activity level of the patient.

Movement disorders, such as tremor, Parkinson's disease, multiple sclerosis, and spasticity may also affect the sleep quality experienced by a patient. The uncontrolled movements, e.g., tremor or shaking, associated such disorders, particularly in the limbs, may cause a patient to experience disturbed sleep. Accordingly, systems according to the invention may monitor sleep quality metrics to determine the state or progression of a movement disorder.

Movement disorders, such as tremor, Parkinson's disease, multiple sclerosis, and spasticity may also affect the overall activity level of a patient. Further, movement disorders are also characterized by irregular, uncontrolled and generally inappropriate movements, e.g., tremor or shaking, particularly of the limbs. In addition to using the sensors described above to sense the overall activity level of a movement disorder patient, some embodiments of the invention may use such sensors to detect the types of inappropriate movements associated with the movement disorder. For example, accelerometers, piezoelectric crystals, or EMG electrodes located in the trunk or limbs of a patient may be able to detect inappropriate movements such as tremor or shaking.

Systems according to the invention may periodically determine the level or severity of such movements based on the signals output by such sensors, associate the inappropriate movement levels with current therapy parameter sets, and determine activity metric values for therapy parameter sets based on the associated levels. For example, a processor of such a system may determine a frequency or amount of time that such movements exceeded a threshold during delivery of a therapy parameter set as an inappropriate movement based activity metric value for the therapy parameter set.

Systems according to the invention may include any of a variety of medical devices that deliver any of a variety of therapies to treat movement disorders, such as DBS, cortical stimulation, or one or more drugs. Baclofen, which may or may not be intrathecally delivered, is an example of a drug that may be delivered to treat movement disorders. Systems may use the techniques of the invention described above to associate any of the above-described sleep quality or activity metrics with therapies or therapy parameter sets for delivery of such therapies. In this manner, such systems may allow a user to evaluate the extent to which a therapy or therapy parameter set is alleviating the movement disorder by evaluating the extent to which the therapy parameter set improves the sleep quality, general activity level, or inappropriate activity level.

The invention is not limited to embodiments in which a programming device receives information from the medical device, or presents information to a user. Other computing devices, such as handheld computers, desktop computers, workstations, or servers may receive information from the medical device and present information to a user as described herein with reference to programmers 20, 26. A computing device, such as a server, may receive information from the medical device and present information to a user via a network, such as a local area network (LAN), wide area network (WAN), or the Internet. Further, in some embodiments, the medical device is an external medical device, and may itself include user interface and display to present activity information to a user, such as a clinician or patient, for evaluation of therapy parameter sets.

As another example, the invention may be embodied in a trial neurostimulator, which is coupled to percutaneous leads implanted within the patient to determine whether the patient is a candidate for neurostimulation, and to evaluate prospective neurostimulation therapy parameter sets. Similarly, the invention may be embodied in a trial drug pump, which is coupled to a percutaneous catheter implanted within the patient to determine whether the patient is a candidate for an implantable pump, and to evaluate prospective therapeutic agent delivery parameter sets. Sleep quality metric values and activity metric values collected during use of the trial neurostimulator or pump may be used by a clinician to evaluate the prospective therapy parameter sets, and select parameter sets for use by the later implanted non-trial neurostimulator or pump. For example, a trial neurostimulator or pump may determine representative values of one or more sleep quality metrics and activity metric values for each of a plurality of prospective therapy parameter sets, and a clinician programmer may present a list of prospective parameter sets and associated representative values to a clinician. The clinician may use the list to identify potentially efficacious parameter sets, and may program a permanent implantable neurostimulator or pump for the patient with the identified parameter sets.

In some embodiments, a therapy delivering implantable or external medical device does not determine whether the patient is attempting to sleep, determine values for sleep quality metrics, determine activity metric values, and/or periodically determine activity levels. Instead, in some embodiments, a computing device, such as one of programming devices 20, 26, or the other types of computing devices identified above, performs one or more of these functions. For example, a programming device, and more particularly a processor of the programming device, e.g., processor 120, may receive physiological parameter values, activity levels, and/or samples of an activity signal from a medical device, and determine activity metric values and sleep quality metric values based on the information received from the medical device using any of the techniques described herein with reference to a medical device.

In some embodiments, the medical device may associate recorded physiological parameter values, signal samples, and/or activity levels with a current therapy parameter set, and may provide information identifying and plurality of therapy parameter sets and collected information associated with the therapy parameter sets to the programming device or other computing device. In such embodiments, the programming device may determine representative sleep quality metric values and activity metric values associated with the various therapy parameter sets using any of techniques described herein with reference to a medical device. The programming device may receive such information from the medical device in real time, or may interrogate the medical device for information recorded by the medical device over a period of time.

Additionally, the invention is not limited to embodiments in which the therapy delivering medical device monitors the physiological parameters of the patient described herein. In some embodiments, a separate monitoring device monitors values of one or more physiological parameters of the patient instead of, or in addition to, a therapy delivering medical device. The monitor may include a processor 46 and memory 48, and may be coupled to or include sensors 40, as illustrated above with reference to an IMD 14 and FIGS. 2A, 2B, and 4. The monitor may determine whether the patient is attempting to sleep, determine values for sleep quality metrics, determine activity metric values, and/or periodically determine activity levels based on the values of the monitored physiological parameter values, or may transmit activity levels or the physiological parameter values to a computing device for determination of whether the patient is attempting to sleep, values for sleep quality metrics, and/or activity metric values.

In embodiments in which the medical device determines sleep quality and activity metric values, the medical device may identify the current therapy parameter set when a value of one or more sleep quality or activity metrics is collected, and may associate that value with the therapy parameter set. In embodiments in which a programming device or other computing device determines activity levels, or activity or sleep quality metric values, the medical device may associate recorded physiological parameter values or activity levels with the current therapy parameter set in the memory. Further, in embodiments in which a separate monitoring device records physiological parameter values, determines activity levels, or determines activity or sleep quality metric values, the monitoring device may mark recorded physiological parameter values, activity levels, or activity or sleep quality metric values with a current time in a memory, and the medical device may store an indication of a current therapy parameter set and time in a memory. A programming device of other computing device may receive indications of the physiological parameter values, activity levels, or activity or sleep quality metric values and associated times from the monitoring device, and indications of the therapy parameter sets and associated times from the medical device, and may associate the physiological parameter values, activity levels, or activity or sleep quality metric values with the therapy parameter set that was delivered by the medical device when the values or levels were recorded.

Figure 12:
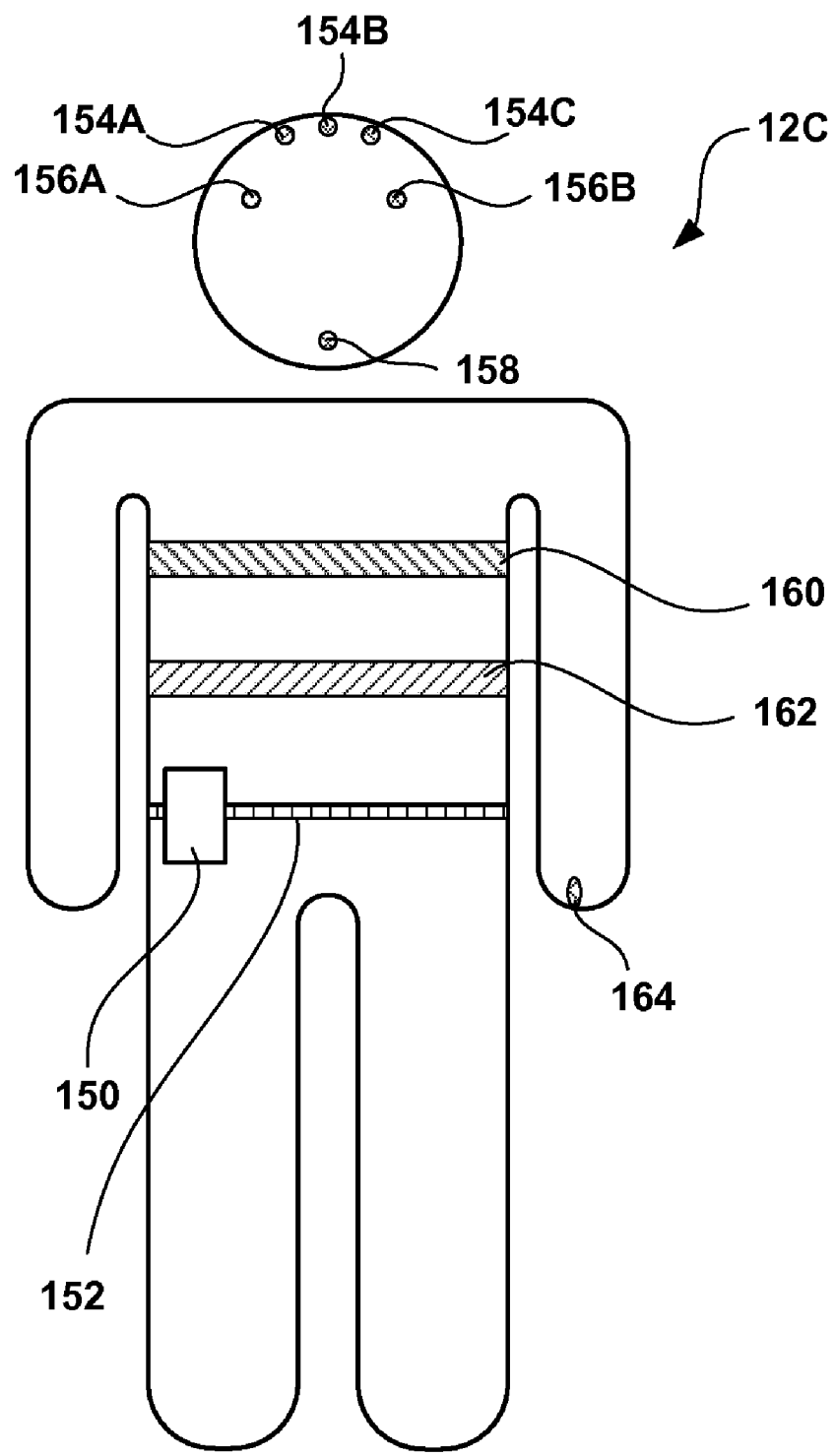
FIG. 12 is a conceptual diagram illustrating a monitor that monitors values of one or more physiological parameters of the patient.

FIG. 12 is a conceptual diagram illustrating a monitor 150 that monitors values of one or more physiological parameters of the patient instead of, or in addition to, a therapy delivering medical device. In the illustrated example, monitor 150 is configured to be attached to or otherwise carried by a belt 152, and may thereby be worn by patient 12C. FIG. 12 also illustrates various sensors 40 that may be coupled to monitor 150 by leads, wires, cables, or wireless connections, such as EEG electrodes 154A-C placed on the scalp of patient 12C, a plurality of EOG electrodes 156A and 156B placed proximate to the eyes of patient 12C, and one or more EMG electrodes 158 placed on the chin or jaw the patient. The number and positions of electrodes 154, 156 and 158 illustrated in FIG. 12 are merely exemplary. For example, although only three EEG electrodes 154 are illustrated in FIGS. 1A and 1B, an array of between 16 and 25 EEG electrodes 114 may be placed on the scalp of patient 12C, as is known in the art. EEG electrodes 154 may be individually placed on patient 12C, or integrated within a cap or hair net worn by the patient.

In the illustrated example, patient 12C wears an ECG belt 160. ECG belt 160 incorporates a plurality of electrodes for sensing the electrical activity of the heart of patient 12C. The heart rate and, in some embodiments, ECG morphology of patient 12C may monitored by monitor 150 based on the signal provided by ECG belt 160. Examples of suitable belts 160 for sensing the heart rate of patient 12C are the "M" and "F" heart rate monitor models commercially available from Polar Electro. In some embodiments, instead of belt 160, patient 12C may wear a plurality of ECG electrodes attached, e.g., via adhesive patches, at various locations on the chest of the patient, as is known in the art. An ECG signal derived from the signals sensed by such an array of electrodes may enable both heart rate and ECG morphology monitoring, as is known in the art.

As shown in FIG. 12, patient 12C may also wear a respiration belt 162 that outputs a signal that varies as a function of respiration of the patient. Respiration belt 162 may be a plethysmograpy belt, and the signal output by respiration belt 162 may vary as a function of the changes is the thoracic or abdominal circumference of patient 12C that accompany breathing by the patient. An example of a suitable belt 162 is the TSD201 Respiratory Effort Transducer commercially available from Biopac Systems, Inc. Alternatively, respiration belt 162 may incorporate or be replaced by a plurality of electrodes that direct an electrical signal through the thorax of the patient, and circuitry to sense the impedance of the thorax, which varies as a function of respiration of the patient, based on the signal. In some embodiments, ECG and respiration belts 160 and 162 may be a common belt worn by patient 12C, and the relative locations of belts 160 and 162 depicted in FIG. 12 are merely exemplary.

In the example illustrated by FIG. 12, patient 12C also wears a transducer 164 that outputs a signal as a function of the oxygen saturation of the blood of patient 12C. Transducer 164 may be an infrared transducer. Transducer 164 may be located on one of the fingers or earlobes of patient 12C. Monitor 150 may additionally or alternatively include or be coupled to any of the variety of sensors 40 described above with reference to FIGS. 2A, 2B, and 4, which output signals which vary as a function of any one or more of activity level, posture, heart rate, ECG morphology, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, brain electrical activity, eye motion, and galvanic skin response, as described above.

Figure 13:
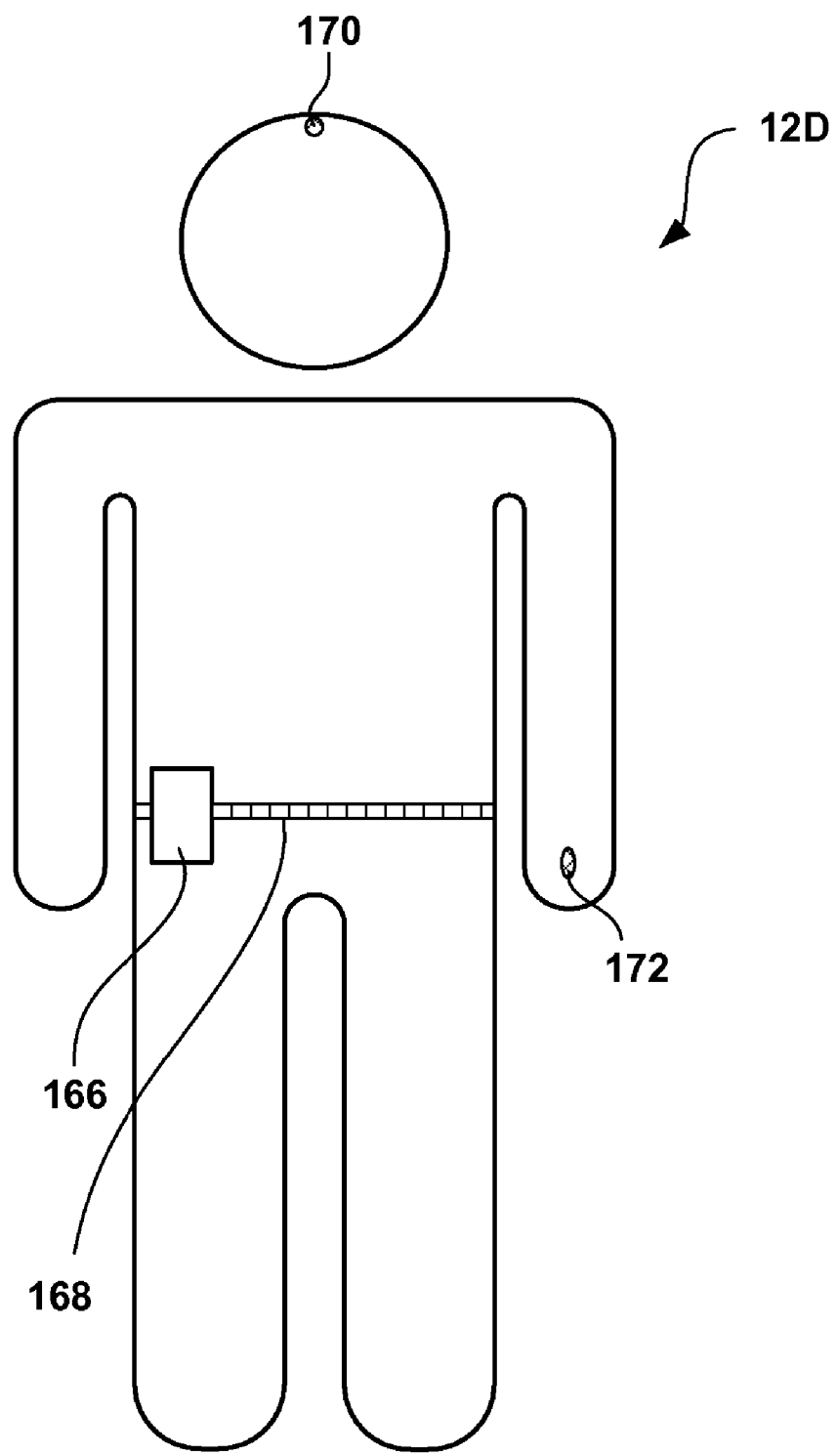
FIG. 13 is a conceptual diagram illustrating a monitor that monitors values of one or more accelerometers of the patient instead of, or in addition to, a therapy delivering medical device.

FIG. 13 is a conceptual diagram illustrating a monitor that monitors values of one or more accelerometers of the patient instead of, or in addition to, such monitoring by a therapy delivering medical device. As shown in FIG. 13, patient 12D is wearing monitor 166 attached to belt 168. Monitor 166 is capable of receiving measurements from one or more sensors located on or within patient 12D. In the example of FIG. 13, accelerometers 170 and 172 are attached to the head and hand of patient 12D, respectively. Accelerometers 170 and 172 may measure movement of the extremities, or activity level, of patient 12D to indicate when the patient moves during sleep or at other times during the day. Alternatively, more or less accelerometers or other sensors may be used with monitor 166.

Accelerometers 170 and 172 may be preferably multi-axis accelerometers, but single-axis accelerometers may be used. As patient 12D moves, accelerometers 170 and 172 detect this movement and send the signals to monitor 166. High frequency movements of patient 12D may be indicative of tremor, Parkinson's disease, or an epileptic seizure, and monitor 166 may be capable of indicating to an IMD 14, for example, that stimulation therapy must be changed to effectively treat the patient. Accelerometers 170 and 172 may be worn externally, i.e., on a piece or clothing or a watch, or implanted at specific locations within patient 12D. In addition, accelerometers 170 and 172 may transmit signals to monitor 166 via wireless telemetry or a wired connection.

Monitor 166 may store the measurements from accelerometers 170 and 172 in a memory. Monitor 166 may analyze the measurements using any of the techniques described herein. In some examples, monitor 146 may transmit the measurements from accelerometers 170 and 172 directly to another device, such as an IMD 14, programming device 20,26, or other computing device. In this case, the other device may analyze the measurements from accelerometers 170 and 172 to detect efficacy of therapy or control the delivery of therapy.

In some examples, a rolling window of time may be used when analyzing measurements from accelerometers 170 and 172. Absolute values determined by accelerometers 170 and 172 may drift with time or the magnitude and frequency of patient 12D movement may not be determined by a preset threshold. For this reason, it may be advantageous to normalize and analyze measurements from accelerometers 170 and 172 over a discrete window of time. For example, the rolling window may be useful in detecting epileptic seizures. If monitor 166 or an IMD 14 detects at least a predetermined number of movements over a 15 second window, an epileptic seizure may be most likely occurring. In this manner, a few quick movements from patient 12D not associated with a seizure may not trigger a response and change in therapy.

Figure 14:
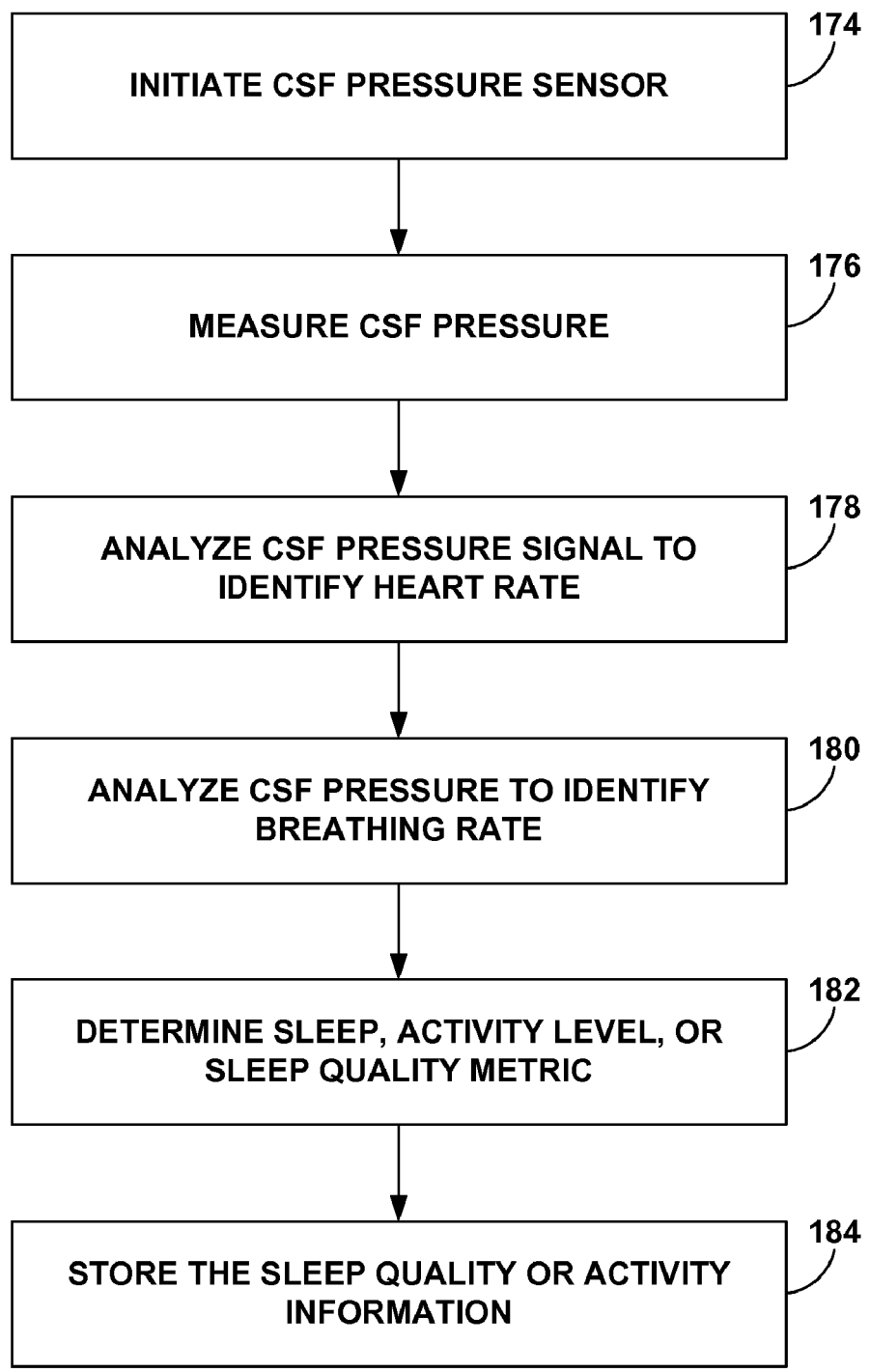
FIG. 14 is a flow diagram illustrating monitoring the heart rate and breathing rate of a patient by measuring cerebral spinal fluid pressure.

FIG. 14 is a flow diagram illustrating monitoring the heart rate and breathing rate of a patient by measuring cerebral spinal fluid pressure. As discussed above, a physiological parameter that may be measured in patient 12D is heart rate and respiration, or breathing, rate. As shown in FIG. 14, cerebral spinal fluid (CSF) pressure may be analyzed to monitor the heart rate and breathing rate of patient 12D. A clinician initiates a CSF pressure sensor to being monitoring heart rate and/or breathing rate (174). Alternatively, the CSF pressure sensor may be implanted within the brain or spinal cord of patient 12D to acquire accurate pressure signals. The CSF pressure sensor must also store the pressure data or begin to transfer pressure data to an implanted or external device. As an example used herein, the CSF pressure sensor transmits signal data to an IMD 14.

Once the CSF pressure sensor is initiated, the CSF pressure sensor measures CSF pressure and transmits the data to an IMD 14 (176). An IMD 14 analyzes the CSF pressure signal to identify the heart rate (178) and breathing rate (180) of patient 12D. The heart rate and breathing rate can be identified within the overall CSF pressure signal. Higher frequency fluctuations (e.g. 40 to 150 beats per minute) can be identified as the heart rate while lower frequency fluctuations (e.g. 3 to 20 breaths per minute) in CSF pressure are the breathing rate. An IMD 14 may employ filters, transformations, or other signal processing techniques to identify the heart rate and breathing rate from the CSF pressure signal.

An IMD 14 may utilize the heart rate and breathing rate information as additional information when determining whether the patient is asleep, determining an activity level, or determining a sleep quality metric for patient 12D (182). For example, faster heart rates and faster breathing rates may indicate that patient 12D is not sleeping. An IMD 14 may then store the sleep or activity information, or use it to adjust stimulation therapy (184).

The invention may also be embodied as a computer-readable medium that includes instructions to cause a processor to perform any of the methods described herein. These and other embodiments are within the scope of the following claims.

The invention claimed is:

1. A medical system comprising:
 a medical device configured to: deliver at least one of a movement disorder therapy, psychological disorder therapy, or deep brain stimulation to a patient, and monitor a plurality of physiological parameters of the patient, wherein the plurality of physiological parameters includes at least one physiological parameter indicative of patient physical activity; and
 a processor configured to: determine when the patient is attempting to sleep, determine values of at least one metric that is indicative of sleep quality based on at least one of the physiological parameters and a determination that the patient is attempting to sleep, periodically determine a value of an activity metric based on at least one of the physiological parameters and a determination that the patient is not attempting to sleep, associate each of the sleep quality and activity metric values with a therapy parameter set that was used by the medical device to deliver the therapy when the metric value was determined, and provide the sleep quality and activity metric values with an indication of the association between the therapy parameter sets and the sleep quality and activity metric values for evaluation of the therapy.

2. The medical system of claim 1, wherein the processor is further configured to: receive sensor measurements from at least one sensor that measures at least one of the plurality of physiological parameters, and determine the value of at least one activity metric based upon the received sensor measurements.

3. The medical system of claim 1, wherein the processor is further configured to: periodically determine an activity level of the patient based on at least one of the physiological parameters, associate each of the activity levels determined when the patient is not attempting to sleep with a therapy parameter set currently used by a medical device when the metric value was determined, and determine an activity metric value for each of a plurality of parameter sets based on activity levels associated with the parameter set.

4. The medical system of claim 1, further comprising at least one sensor configured to generate a cerebral spinal fluid (CSF) pressure signal, wherein the processor is further configured to: receive the CSF pressure signal and identify at least one of a heart rate and a breathing rate from the CSF pressure signal.

5. A medical system comprising:
 a medical device configured to: deliver at least one of a movement disorder therapy, psychological disorder therapy, or deep brain stimulation to a patient, and monitor a plurality of physiological parameters of the patient, wherein the plurality of physiological parameters includes at least one physiological parameter indicative of patient physical activity;
 a processor configured to: determine when the patient is attempting to sleep, determine values of at least one metric that is indicative of sleep quality based on at least one of the physiological parameters and a determination that the patient is attempting to sleep, periodically determine a value of an activity metric based on at least one of the physiological parameters and a determination that the patient is not attempting to sleep, associate each of the sleep quality and activity metric values with a therapy parameter set that was used by the medical device to deliver the therapy when the metric value was determined, and provide the sleep quality and activity metric values with an indication of the association between the therapy parameter sets and the sleep quality and activity metric values for evaluation of the therapy; and
 a module configured to identify at least one sleep state based on a frequency of an electroencephalogram (EEG) signal of the patient, wherein the processor is further configured to determine the value of the at least one metric that is indicative of sleep quality based upon the at least one identified sleep state.

6. The medical system of claim 5, wherein the module is configured to identify at least one of an S3 and S4 sleep state.

7. The medical system of claim 1, further comprising a computing device including a display configured to present a list of the therapy parameter sets, associated representative sleep quality metric values, and associated activity metric values.

8. The medical system of claim 7, wherein the computing device is configured to: receive user selection of one of the sleep quality metrics and activity metric, and order the list of therapy parameter sets according to values of the user selected one of the sleep quality metrics and activity metrics.

9. The medical system of claim 1, wherein the medical device comprises an implantable medical device.

10. The medical system of claim 1, wherein the medical device comprises at least one of an implantable neurostimulator or an implantable pump.

11. The medical system of claim 1, wherein the processor comprises a processor of the medical device.

12. A medical system comprising:
a medical device configured to: deliver a therapy to a patient according to therapy parameters that change over time according to a plurality of therapy parameter sets, and monitor a plurality of physiological parameters of the patient, wherein the plurality of physiological parameters includes at least one physiological parameter indicative of patient physical activity; and
processor configured to:
determine when the patient is attempting to sleep,
determine values of at least one metric that is indicative of sleep quality based on at least one of the physiological parameters and a determination that the patient is attempting to sleep,
periodically determine a value of an activity metric based on at least one of the physiological parameters and a determination that the patient is not attempting to sleep,
associate, for each therapy parameter set in the plurality of therapy parameter sets, each of the sleep quality and activity metric values that occurred during the delivery of the therapy to the patient according that therapy parameter set with that therapy parameter set, and
provide, for each therapy parameter set in the plurality of therapy parameter sets, the sleep quality and activity metric values associated with that individual therapy parameter set with an indication of the association between that individual therapy parameter set and the sleep quality and activity metric values associated with that individual therapy parameter set to a user in a manner that is indicative of efficacy of that individual therapy parameter set.

* * * * *